(12) United States Patent
Barberio

(10) Patent No.: US 11,654,039 B2
(45) Date of Patent: May 23, 2023

(54) TUBULAR VENTING DEVICE FOR SURGICAL CASTS AND OTHER ORTHOPEDIC DEVICES

(71) Applicant: Alessandro Barberio, Aurora (CA)

(72) Inventor: Alessandro Barberio, Aurora (CA)

( * ) Notice: Subject to any disclaimer, the term of this patent is extended or adjusted under 35 U.S.C. 154(b) by 310 days.

(21) Appl. No.: 16/957,828

(22) PCT Filed: Dec. 24, 2018

(86) PCT No.: PCT/CA2018/051668
§ 371 (c)(1),
(2) Date: Jun. 25, 2020

(87) PCT Pub. No.: WO2019/126875
PCT Pub. Date: Jul. 4, 2019

(65) Prior Publication Data
US 2021/0059850 A1   Mar. 4, 2021

Related U.S. Application Data

(60) Provisional application No. 62/708,796, filed on Dec. 26, 2017, provisional application No. 62/762,335, (Continued)

(51) Int. Cl.
*A61F 13/04* (2006.01)
*B32B 1/08* (2006.01)
(Continued)

(52) U.S. Cl.
CPC ........ *A61F 5/05858* (2013.01); *A61F 5/0118* (2013.01); *A61F 5/05825* (2013.01);
(Continued)

(58) Field of Classification Search
None
See application file for complete search history.

(56) References Cited

U.S. PATENT DOCUMENTS 3,701,349 A * 10/1972 Larson ............... A61F 5/05816
602/14
4,308,862 A * 1/1982 Kalmar ............... A61F 13/046
602/14
(Continued)

FOREIGN PATENT DOCUMENTS

CA    2355041 A1 * 10/2002
CA    2478159 A1 *  2/2006 ........... A61F 13/041
(Continued)

*Primary Examiner* — Jeffrey A Vonch
(74) *Attorney, Agent, or Firm* — Christopher J. Dynowski; Ryan W. Dupuis; Ade & Company Inc.

(57) ABSTRACT

Described is a venting device including a flexible outer covering defining an outer surface and an inner surface, a set of helicoidal venting strips, and a set of helicoidal buffers. The outer covering has a first end and a second end and a longitudinal axis therebetween. Each venting strip is anchored to the inner surface and extends substantially between the first end and the second end and the set of venting strips is arranged substantially helicoidal and defines a set of helicoidal seams therebetween. The set of helicoidal buffers includes a buffer covering an inner opening of each seam of the set of helicoidal seams where each buffer is configured to shield the inner opening of the corresponding seam from penetration and each buffer is anchored to at least one of the outer covering and a neighbouring venting strip of the set of venting strips.

14 Claims, 33 Drawing Sheets

Related U.S. Application Data filed on May 1, 2018, provisional application No. 62/761,926, filed on Apr. 13, 2018, provisional application No. 62/917,348, filed on Dec. 4, 2018, provisional application No. 62/917,589, filed on Dec. 17, 2018.

(51) Int. Cl.

| | | |
|---|---|---|
| *B32B 3/24* | (2006.01) | |
| *B32B 3/30* | (2006.01) | |
| *B32B 5/02* | (2006.01) | |
| *B32B 7/09* | (2019.01) | |
| *B32B 7/12* | (2006.01) | |
| *A61F 5/058* | (2006.01) | |
| *A61F 5/01* | (2006.01) | |
| *B32B 3/08* | (2006.01) | |
| *B32B 3/26* | (2006.01) | |
| *B32B 27/12* | (2006.01) | |
| *B32B 3/18* | (2006.01) | |
| *B32B 1/04* | (2006.01) | |
| *B32B 5/06* | (2006.01) | |
| *B32B 5/26* | (2006.01) | |

(52) U.S. Cl.
CPC .......... *A61F 13/041* (2013.01); *A61F 13/046* (2013.01); *B32B 1/04* (2013.01); *B32B 1/08* (2013.01); *B32B 3/08* (2013.01); *B32B 3/18* (2013.01); *B32B 3/266* (2013.01); *B32B 3/30* (2013.01); *B32B 27/12* (2013.01); *B32B 5/06* (2013.01); *B32B 5/26* (2013.01); *B32B 7/09* (2019.01); *B32B 7/12* (2013.01); *B32B 2307/724* (2013.01); *B32B 2535/00* (2013.01); *Y10T 428/139* (2015.01); *Y10T 428/1352* (2015.01); *Y10T 428/1362* (2015.01); *Y10T 428/1366* (2015.01); *Y10T 428/1369* (2015.01); *Y10T 428/1376* (2015.01); *Y10T 428/1393* (2015.01); *Y10T 428/19* (2015.01); *Y10T 428/192* (2015.01); *Y10T 428/193* (2015.01); *Y10T 428/23* (2015.01); *Y10T 428/24322* (2015.01); *Y10T 428/24331* (2015.01); *Y10T 428/24562* (2015.01); *Y10T 428/24612* (2015.01); *Y10T 428/24752* (2015.01)

(56) References Cited

U.S. PATENT DOCUMENTS

| | | | | |
|---|---|---|---|---|
| 5,527,265 | A | * | 6/1996 | McKeel ............... A61F 13/041 602/5 |
| 5,720,714 | A | * | 2/1998 | Penrose .................... B32B 3/30 602/42 |
| 5,916,184 | A | * | 6/1999 | McKeel ............... A61F 13/046 602/5 |
| 6,547,751 | B1 | * | 4/2003 | Barberio ............. A61F 13/046 602/14 |
| 6,616,622 | B1 | * | 9/2003 | Barberio ............. A61F 13/046 602/5 |
| 7,250,034 | B2 | | 7/2007 | Barberio |
| 7,311,685 | B1 | * | 12/2007 | Policastro, Jr. .......... A61F 13/06 602/5 |
| 2004/0230148 | A1 | * | 11/2004 | Barberio ............. A61F 13/041 602/3 |
| 2005/0059915 | A1 | * | 3/2005 | Dunagan ............. A61F 13/046 602/14 |
| 2005/0228322 | A1 | * | 10/2005 | Stanton ................ A61L 15/24 602/3 |
| 2006/0155226 | A1 | * | 7/2006 | Grim .................... A61F 13/041 602/8 |
| 2006/0213612 | A1 | * | 9/2006 | Perron ................ B29C 66/919 156/304.3 |
| 2008/0082035 | A1 | * | 4/2008 | Evans .................... D04B 21/16 602/60 |
| 2008/0196136 | A1 | * | 8/2008 | Fellouhe ........... B29C 66/91421 2/243.1 |
| 2008/0287852 | A1 | * | 11/2008 | Evans .................... D04B 1/126 602/43 |
| 2009/0036999 | A1 | * | 2/2009 | Egilsson ................ A61L 27/26 623/36 |
| 2009/0198160 | A1 | * | 8/2009 | Coyne .................. A61F 13/046 602/2 |
| 2011/0152735 | A1 | | 6/2011 | Barberio |
| 2012/0128943 | A1 | * | 5/2012 | Wangbunyen ...... B29C 65/5042 156/73.4 |
| 2014/0052041 | A1 | * | 2/2014 | Barberio ........... A61F 13/00042 604/385.01 |
| 2014/0343471 | A1 | * | 11/2014 | Barberio .................. A61F 5/05 602/14 |
| 2016/0324666 | A1 | * | 11/2016 | Barberio .................. A61F 2/80 |
| 2018/0296394 | A1 | * | 10/2018 | Barberio ........... A61F 13/00029 |

FOREIGN PATENT DOCUMENTS

| | | | | |
|---|---|---|---|---|
| DE | 3820098 A | * | 12/1989 | .......... A61F 13/046 |
| EP | 0346697 A2 | * | 12/1989 | |
| WO | WO-9603100 A1 | * | 2/1996 | ......... A61F 13/0273 |
| WO | WO-2006136024 A1 | * | 12/2006 | .......... A61F 13/046 |
| WO | WO-2017059533 A1 | * | 4/2017 | ....... A61F 13/00029 |

* cited by examiner

TUBULAR VENTING DEVICE FOR SURGICAL CASTS AND OTHER ORTHOPEDIC DEVICES

FIELD OF THE INVENTION

The present specification relates generally to venting devices, and specifically to venting devices for surgical casts and other orthopedic devices.

BACKGROUND OF THE INVENTION

The adequate ventilation of human skin or other animal skin is often desirable. For example, if a patient has a broken bone in their arm they will often receive a cast on the arm to assist in the healing process. However, a cast or other covering over skin can often result in heat buildup, bacterial buildup and related discomfort.

Venting of skin can be achieved by providing a path between ambient air and the skin which is substantially open to the passage of air. However, while a variety of known ventilation devices can be used, many continue to seek an easily-applied venting device which can be readily produced and transported.

SUMMARY OF THE INVENTION

In an embodiment of the present invention, there is provided a venting device, comprising: a flexible outer covering defining an outer surface and an inner surface, the outer covering defining a first end and a second end and a longitudinal axis therebetween; a set of helicoidal venting strips, each venting strip anchored to the inner surface and extending substantially between the first end and the second end, the set of venting strips arranged substantially helicoidal and defining a set of helicoidal seams therebetween; a set of helicoidal buffers, the set of helicoidal buffers including a buffer covering an inner opening of each seam of the set of helicoidal seams, each buffer configured to shield the inner opening of the corresponding seam from penetration, each buffer anchored to at least one of the outer covering and a neighbouring venting strip of the set of venting strips.

BRIEF DESCRIPTION OF THE DRAWINGS

The principles of the invention may better be understood with reference to the accompanying figures provided by way of illustration of an exemplary embodiment, or embodiments, incorporating principles and aspects of the present invention, and in which.

DETAILED DESCRIPTION OF THE EMBODIMENTS

Figure 1:
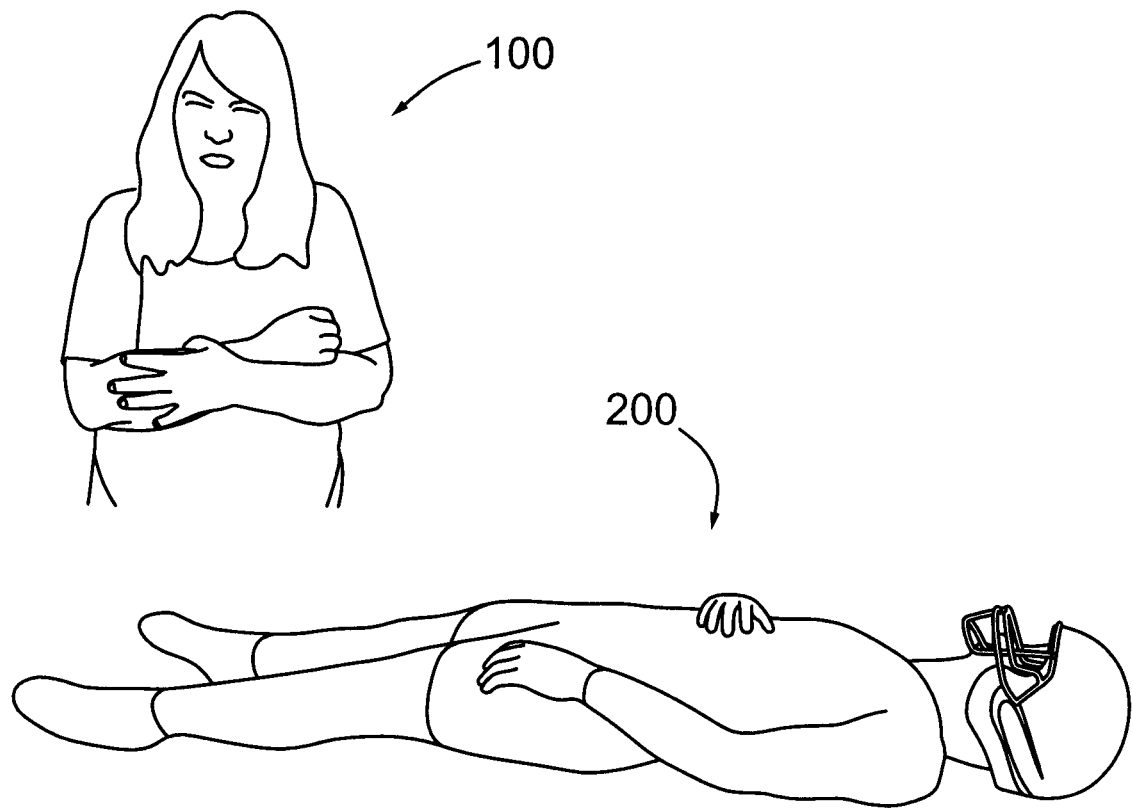
FIG. 1 is a schematic diagram of an injured person standing up and a schematic diagram of an injured person lying down.

The description that follows, and the embodiments described therein, are provided by way of illustration of an example, or examples, of particular embodiments of the principles of the present invention. These examples are provided for the purposes of explanation, and not of limitation, of those principles and of the invention. In the description, like parts are marked throughout the specification and the drawings with the same respective reference numerals. The drawings are not necessarily to scale and in some instances proportions may have been exaggerated in order more clearly to depict certain features of the invention.

Priority is claimed to U.S. provisional patent application No. 62/708,796, filed Dec. 26, 2018, U.S. provisional patent application No. 62/761,926 filed Apr. 13, 2018, U.S. provisional patent application No. 62/762,335 filed May 1, 2018, a United States provisional patent application mailed to the United States Patent and Trademark Office on Nov. 30, 2018 by the present applicant and entitled IMPROVED TUBULAR VENTING DEVICE FOR SURGICAL CASTS AND OTHER ORTHOPEDIC DEVICES, and a United States provisional patent application mailed to the United States Patent and Trademark Office on Dec. 14, 2018 by the present applicant and entitled IMPROVED TUBULAR VENTING DEVICE FOR SURGICAL CASTS AND OTHER ORTHOPEDIC DEVICES, each of which are hereby incorporated by reference.

An aspect of this description relates to a venting device for use in covering a surface of skin. An aspect of this description relates to a venting device for use between the skin of a patient and a covering. An aspect of this description relates to a venting device for use under a cast or sling or brace or splint or compression device.

Figure 2:
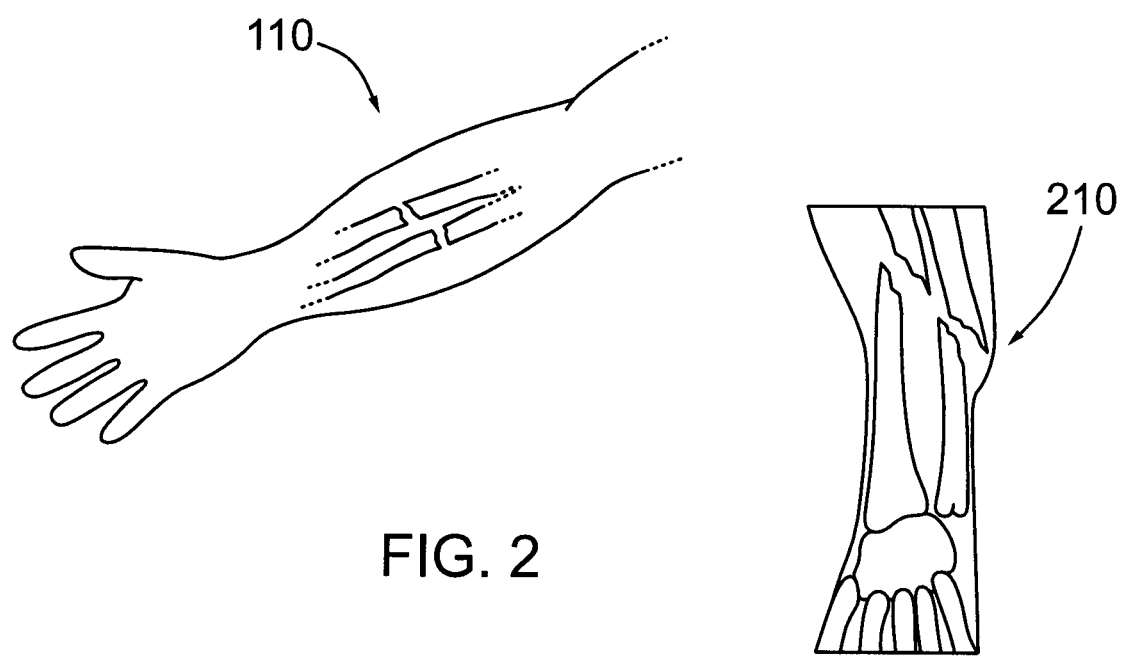
FIG. 2 is a schematic diagram of a first broken arm and a schematic diagram of a second broken arm.

In the below, embodiments of a venting device are described in relation to casts and slings mounted on an arm of a user. FIG. 1 depicts a first user 100 and a second user 200, and FIG. 2 depicts a first user arm 110 and a second user arm 210. When a bone in an arm or other limb of an individual is broken, treatment often involves the application of a cast or the use of a sling or the application of a compression device.

Figure 3:
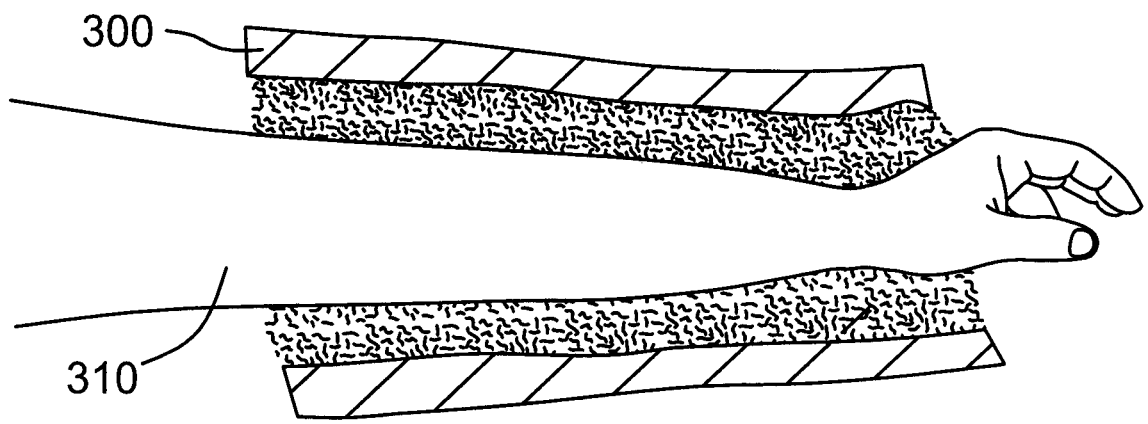
FIG. 3 is a schematic cutaway diagram of a cast mounted on an arm, a perspective view of a cast mounted on an arm, and a schematic diagram of a thermostat indicating an increasing temperature.
Figure 3:
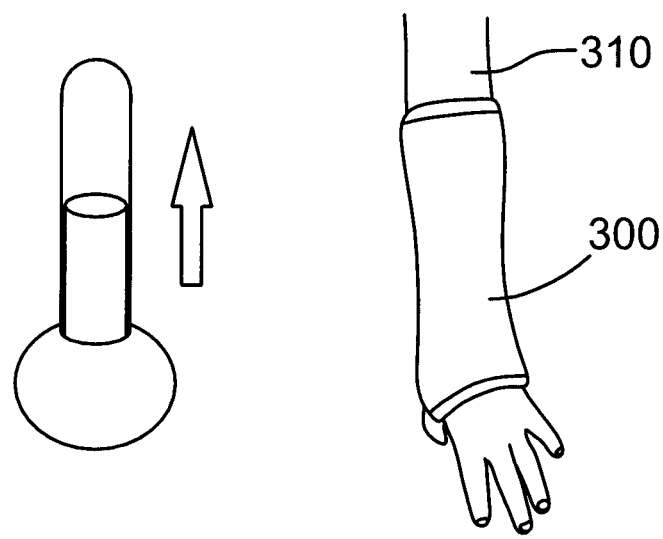

An example of an immobilizing fiberglass cast is depicted in FIG. 3. Cast 300 is applied to arm 310. As often happens with an immobilizing cast, heat, odour, and bacteria are trapped between arm 310 and cast 300.

Figure 4:
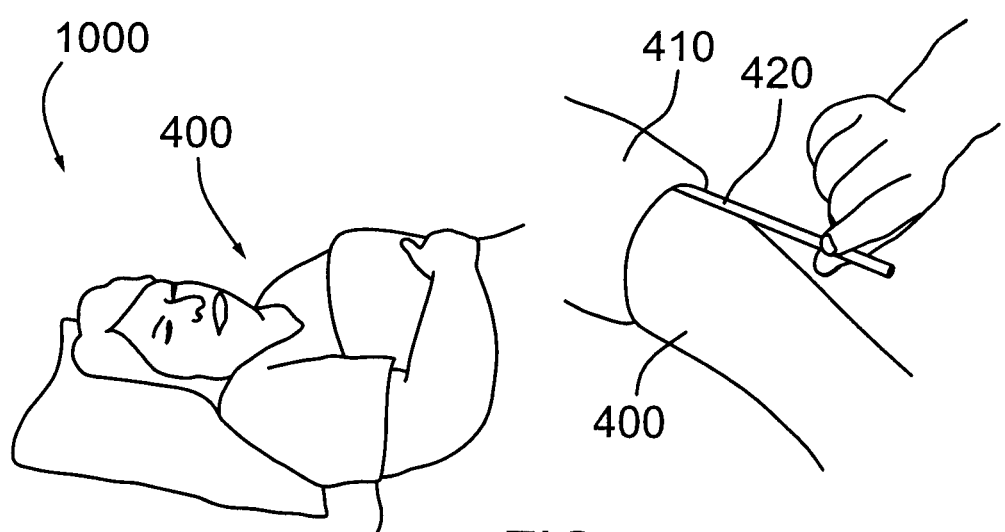
FIG. 4 is a schematic diagram of a suffering patient and a schematic diagram of a venting operation.

As depicted in FIG. 4, trapped heat, odour, or bacteria can cause discomfort to patient 400 on whom a cast 410 is mounted. As a result, patient 400 may attempt to relieve the discomfort by inserting a probing object 420 under cast 410.

Figure 5:
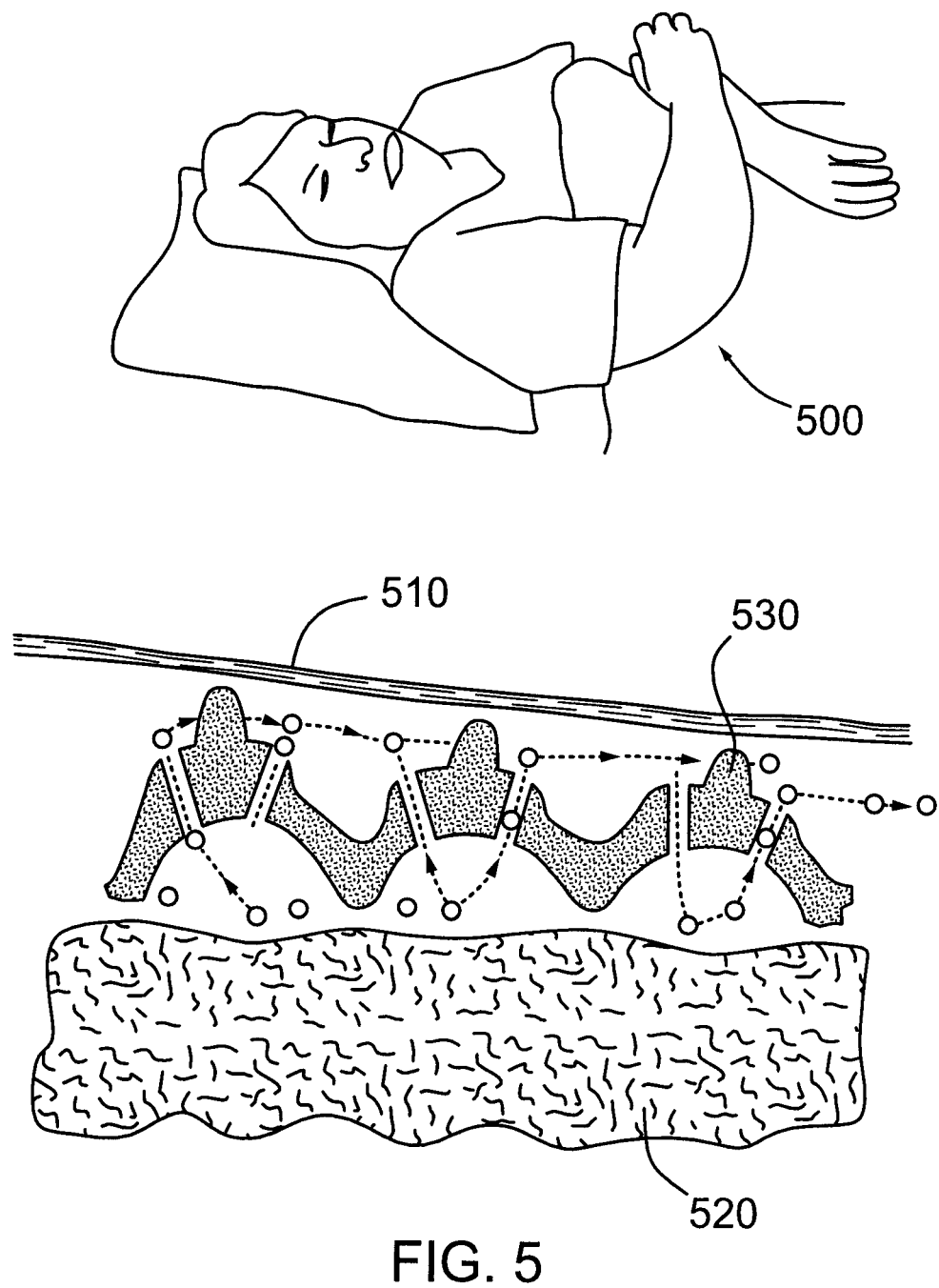
FIG. 5 is a schematic view of an injured patient and a cross sectional view of a venting apparatus resting on a forearm under a cast.

However, if a venting device is used underneath a cast, much discomfort can be alleviated. For example, user 500 of FIG. 5 is wearing cast 510 on arm 520, but venting device 530 has been placed between cast 510 and arm 520 to maintain a venting space between the cast and the arm through which venting air may pass. Venting devices increase air flow beneath a cast and help to reduce bacteria, heat, and odour buildup.

While venting devices are depicted and described herein in use with casts and slings, it is to be understood that venting devices could also be used alone, could be modified to include inherent elements such as cast or sling-like elements, or could be used with other devices such as compression devices.

Figure 6:
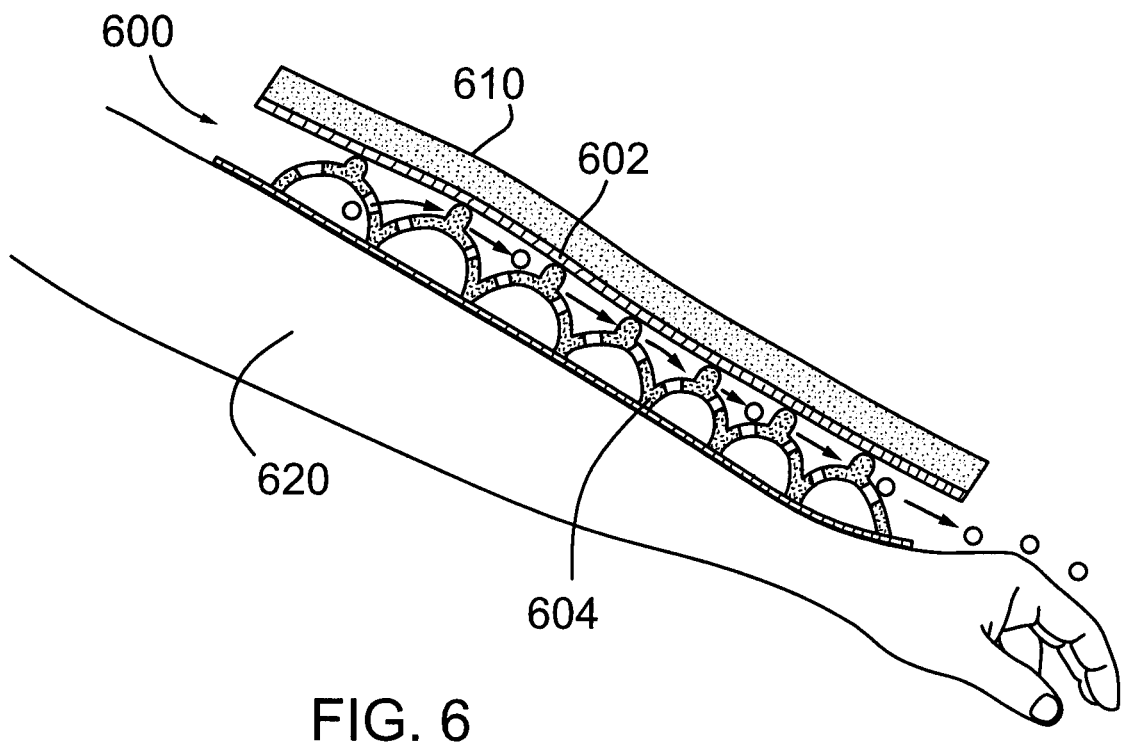
FIG. 6 is a cut away view of a venting apparatus mounted on an arm under a cast, according to an embodiment.
Figure 7:
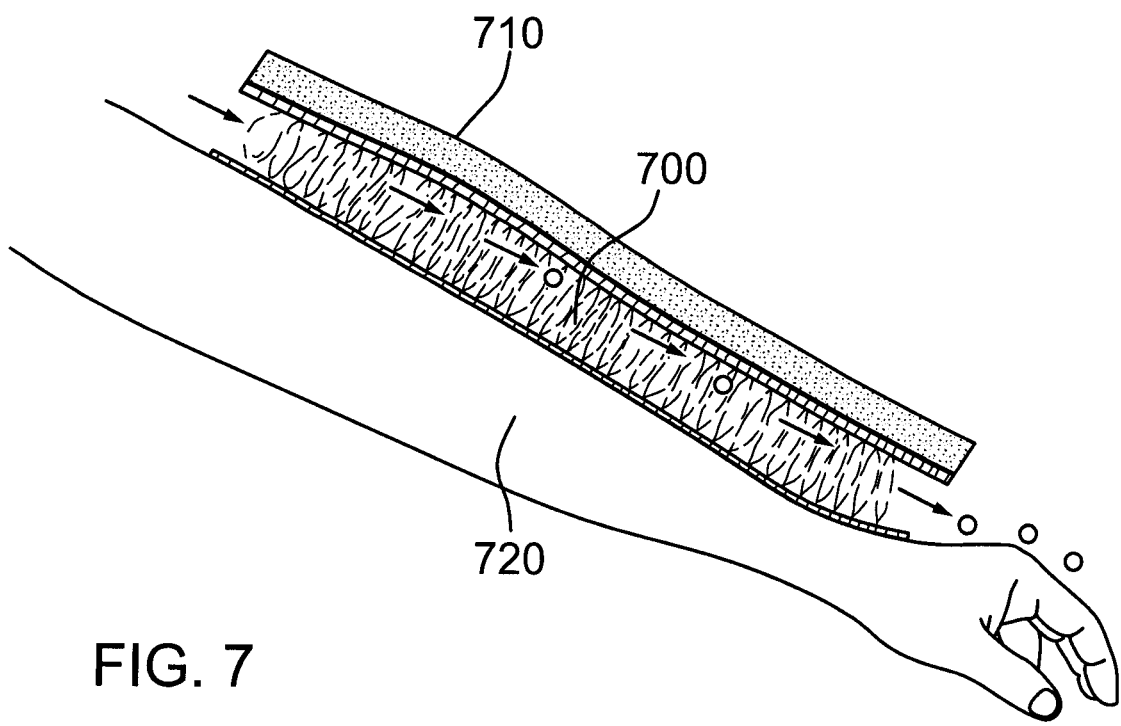
FIG. 7 is a cut away view of a venting apparatus mounted on an arm under a cast, according to an embodiment.

A variety of materials and configurations may be used to form a venting device, provided the device assists in defining a venting space through which venting air may pass. FIGS. 6 and 7 depict two venting materials which may be used, a protrusion layer and a fabric-spacer layer, respectively. Venting material, such as fabric-spacer material, may be designed in some embodiments to be stretchable in four ways, but two ways (lengthwise and widthwise) will do in some embodiments.

Venting device 600 of FIG. 6 is mounted between cast 610 and arm 620. Venting device 600 includes a protrusion material which includes a protrusion sheet 604 and a cover sheet 602, discussed further below. Venting device 700 of FIG. 7 is mounted between cast 710 and arm 720. Venting device 700 includes a fabric-spacer material, discussed further below.

Figure 8:
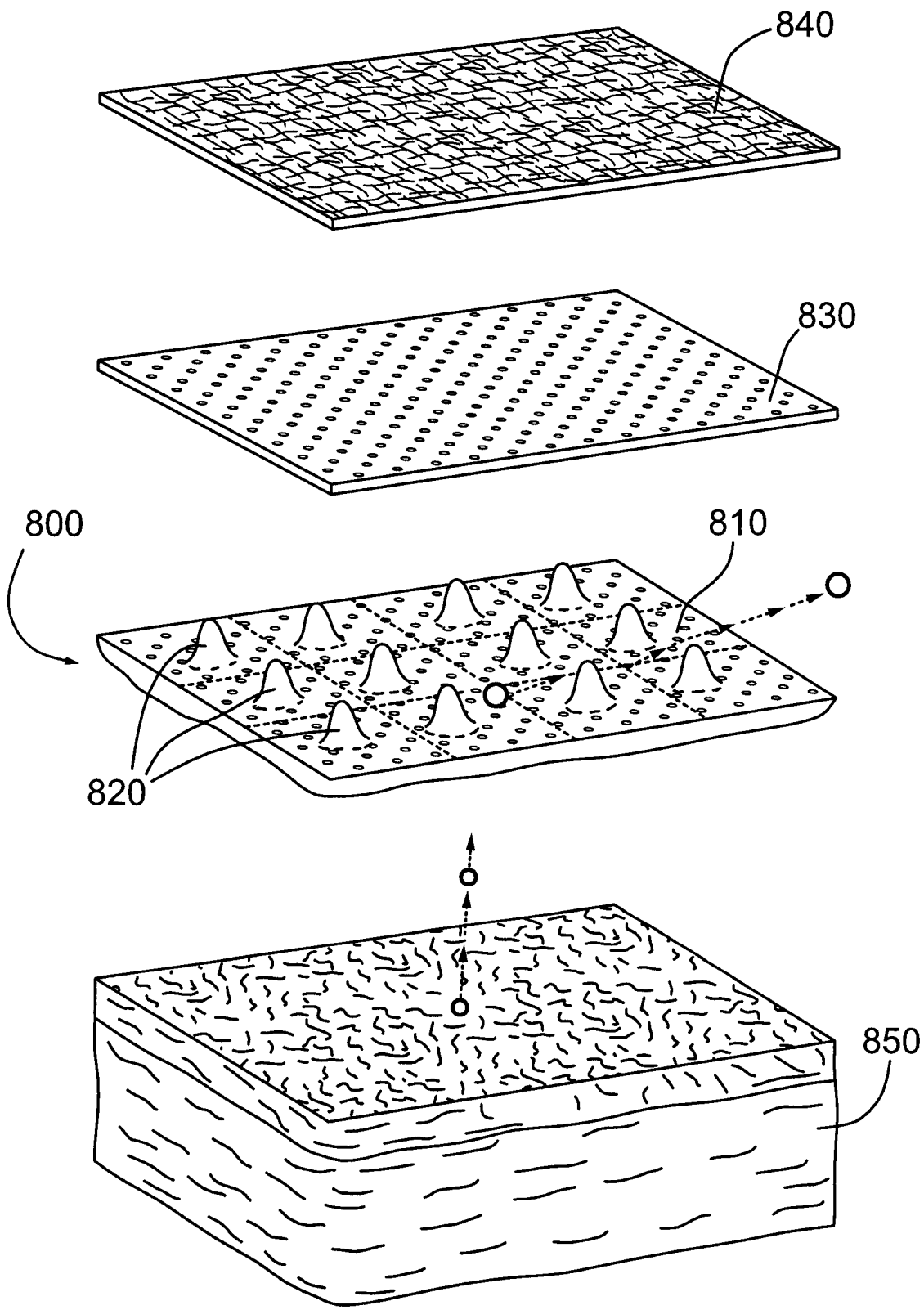
FIG. 8 is an exploded view of a venting apparatus mounted on an arm under a cast, according to an embodiment.

FIG. 8 shows an exploded view of a venting device incorporating a protrusion material. Protrusion material 800 includes a protrusion sheet 810 forming a plurality of protrusions 820, each protrusion 820 corresponding to an underside cavity (not shown). Protrusion material 800 also includes a cover sheet 830, the protrusion layer and the cover sheet defining a venting space therebetween. The protrusion material 800 is placed between cast 840 and skin 850 to allow air to pass between cast 840 and skin 850. Sheets 810 and 830 are perforated to allow for easy air circulation. Sheets of a protrusion layer, such as 810 and 830, may be formed of medical silicone or thermoformable material, for example. In some embodiments, protrusions of a protrusion material must be strong enough to withstand external pressures. In some embodiments, the protrusions of a protrusion material are domed or partially domed with a cavity on the opposing side. In various embodiments, protrusions can be round, square, rectangular, or any geometric shape, or a combination of shapes. In some embodiments, the cavities formed opposite protrusions are designed to be interfacing with the skin of a user to provide a smooth and comfortable resting cushioning surface. In some embodiments, a protrusion sheet and a cover sheet are free to move relative one another, such as free to shift within the limits of an envelop such as the tubinette described below. In some embodiments, a protrusion sheet and a cover sheet are secured to one another and not free to move relative one another. In some embodiments, no cavity is provided opposite a protrusion, however a cavity is preferred.

Figure 9:
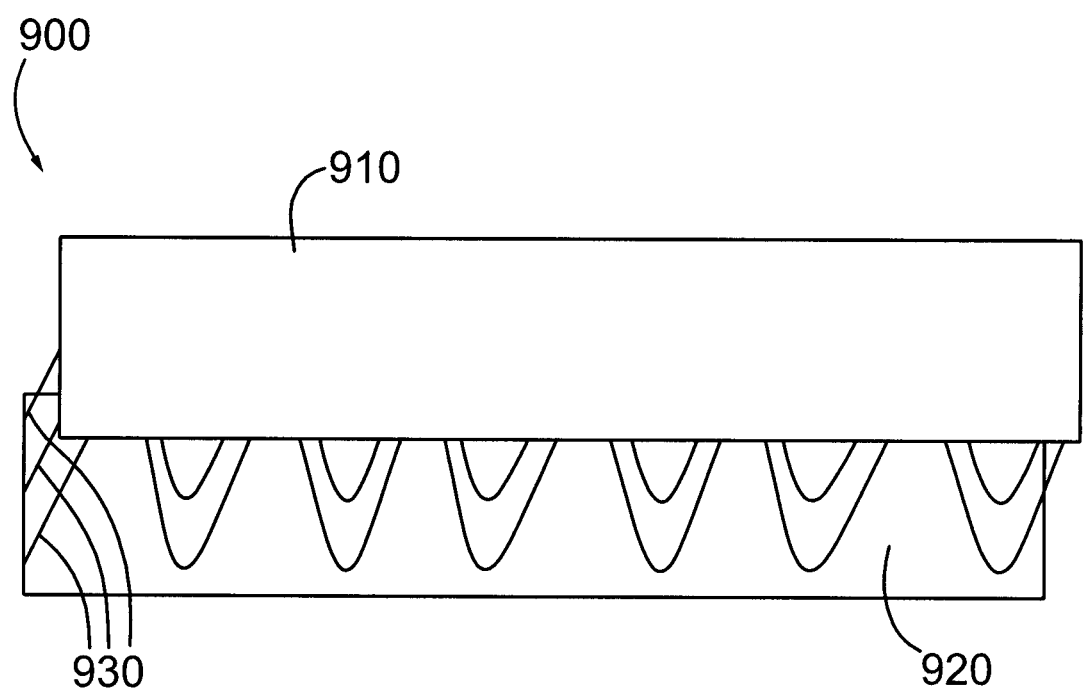
FIG. 9 is a partial cross-sectional view of a fabric buffer material, a cross sectional view of a fabric buffer material, and a schematic view of a resiliency test of a fabric buffer material.

FIG. 9 shows further details of a fabric-spacer material. Fabric-spacer material 900 of FIG. 9 has a top layer 910 and a bottom layer 920 separated by a set of threads or fabric elements 930. The set of threads or fabric elements 930 includes threads of varying resiliency to vary the anticipated density and height of device 900 when placed over a user's skin. Top and bottom layers 910 and 920 are porous fabric layers allowing air circulation. Fabric-spacer material may be made, for example, of hypoallergenic polyester or nylon. Fabric-spacer material is generally lighter and less expensive than protrusion material.

Fabric-spacer materials are used in many applications such as tennis shoes, backpacks, car seat cushions, and bras. Fabric-spacer materials can often be designed for particular uses, such as by varying the resiliency of interior materials, top layer materials or bottom layer materials. In some embodiments, a fabric-spacer venting strip has a surface treatment to apply non-slip silicone or anti-bacterial coating or adhesive or a combination.

In some embodiments, fabric-spacer materials are used which are designed to have a high air permeability, such as a permeability of more than 5 cubic feet per minute, more than 50 cubic feet per minute, or more than 90 cubic feet per minute.

In some embodiments of the present invention a venting device is formed which includes an outer tubular flexible covering, such as a netting or similar, for use in anchoring a set of strips of venting material separated from one another by buffers. Buffers assist in allowing the use of venting devices having a plurality of venting strips without the risk that poor application of the venting devices results in the skin of a user being pinched between venting strips. In some embodiments, buffers are perforated through one or more panels of the buffer to permit air, such as atmospheric or environmental air, to pass. In some embodiments, buffers are extruded. In some embodiments, buffers are formed of flexible, hypoallergenic, and hydrophilic material. In some embodiments, buffers are thermoformed buffers or include thermoformed flexible solid protrusions. In some embodiments, a buffer is made of medical silicone, ethyl vinyl acetate ("EVA"), polyester, gel, foam, Plastazote™, polyurethane or another hypoallergenic and flexible substitute or a combination of the above.

Figure 10:
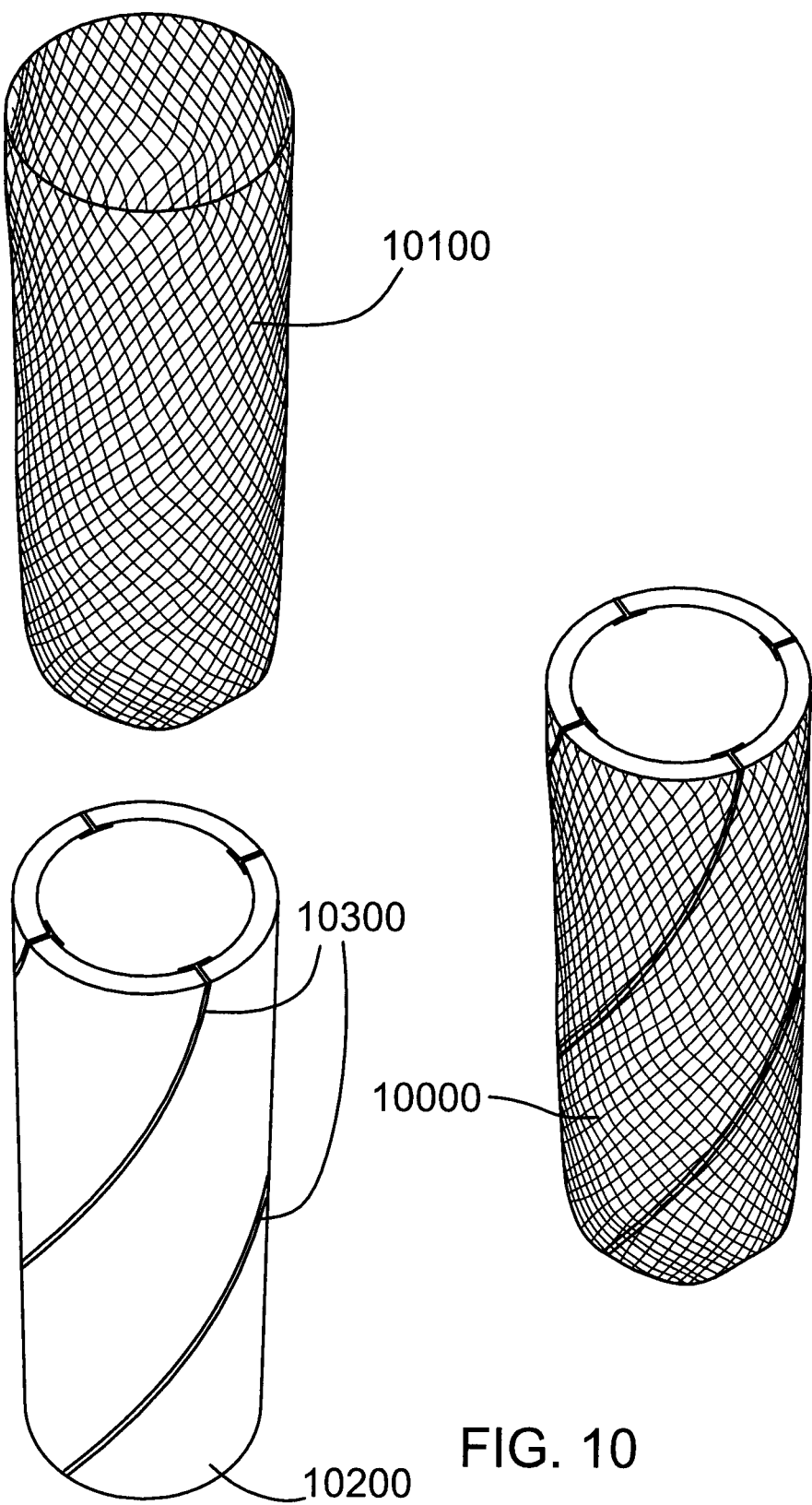
FIG. 10 is a perspective view of an outer cover, a perspective view of a set of buffers and venting strips, and a perspective view of a venting apparatus, according to an embodiment.

FIG. 10 depicts an embodiment of a venting device 10000. Venting device 10000 includes an outer netting 10100 formed into a tubular outer covering. Venting device 10000 also includes a set of strips of venting material 10200 separated by a set of buffers 10300. The set of strips of venting material 10200 and the set of buffers 10300 are covered by outer netting 10100 and each independently secured to outer netting 10100. Independent securing of each strip and buffer allows the strips and buffers to shift relative to neighbouring strips and buffers when the venting device 10000 is twisted. In some embodiments, an outer covering is a netting or other elastic material. In some embodiments, an outer cover is a tube of flexible material. In some embodiments, an outer covering is a tubular expandable stockinette.

Twisting of the venting device 10000 may be used to adjust a standardized size for use with a particular limb or other vented subject. For example, venting device 10000 may be manufactured in a number of standard sizes. In some embodiments, when a venting device is needed an appropriate size is selected, a limb or other vented subject is inserted into the venting device, and the venting device is then twisted to modify the shape of the venting device to match the contours of the limb or other vented subject. In some embodiments, once the venting device is applied to a limb or other vented subject to substantially match the contours of the limb or other vented subject, the venting device is secured to the vented subject or an adjacent surface, such as via surgical adhesive tape, to hold the venting device in the desired position. In some embodiments, once a venting device is applied and secured, a cast, compression device, sling, or related apparatus is applied over the venting device. In some embodiments, larger venting devices are used for adults, smaller ones for children, larger ones for torsos, smaller ones for arms, and custom ones in some situations.

In some embodiments, a venting device can also be squeezed to assist in having the venting device match the contours of a vented subject, in addition to or as an alternative to twisting. For example, a venting device can be squeezed to an appropriate shape and then a cast or other covering added to cover it and hold it in the squeezed position.

Figure 11:
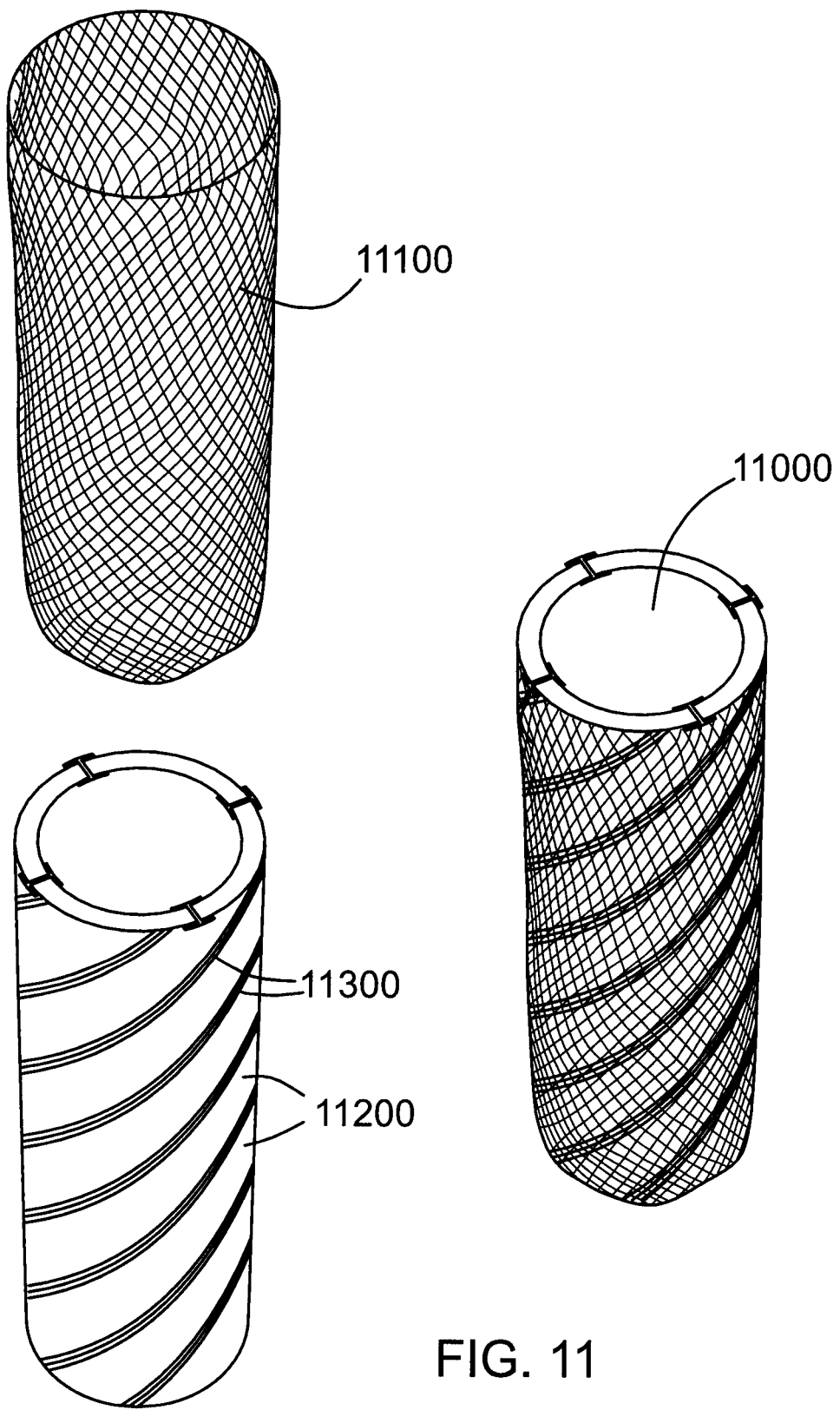
FIG. 11 is a perspective view of an outer cover, a perspective view of a set of buffers and venting strips, and a perspective view of a venting apparatus, according to an embodiment.

FIG. 11 depicts another example of a venting device. Venting device 11000 includes an outer netting 11100, inside the outer netting 11100 a set of venting strips 11200 and buffers 11300 are secured. Buffers 11300 are 'H' shaped buffers having a separation panel between a lower shielding panel and an upper securing panel, as will be discussed further below.

While strips of venting material such as fabric-spacer material or protrusion material may be anchored directly to an outer covering in a venting device, they may also be contained in a fabric or netting of their own which is in turn anchored to the outer covering of the venting device. In some embodiments, each strip of venting material is contained in a tubinette, such as a tubinette formed of netting or loose fabric. In some embodiments, a tubinette is a protective, hydrophilic tubinette. In some embodiments, a tubinette includes a moisture absorbent, porous, cotton fabric. In some embodiments, a strip of venting material is enclosed in a tubinette but not otherwise secured to the tubinette, such as to leave the strip of venting material free to shift within the tubinette to allow for easier twisting of a venting device.

Figure 12:
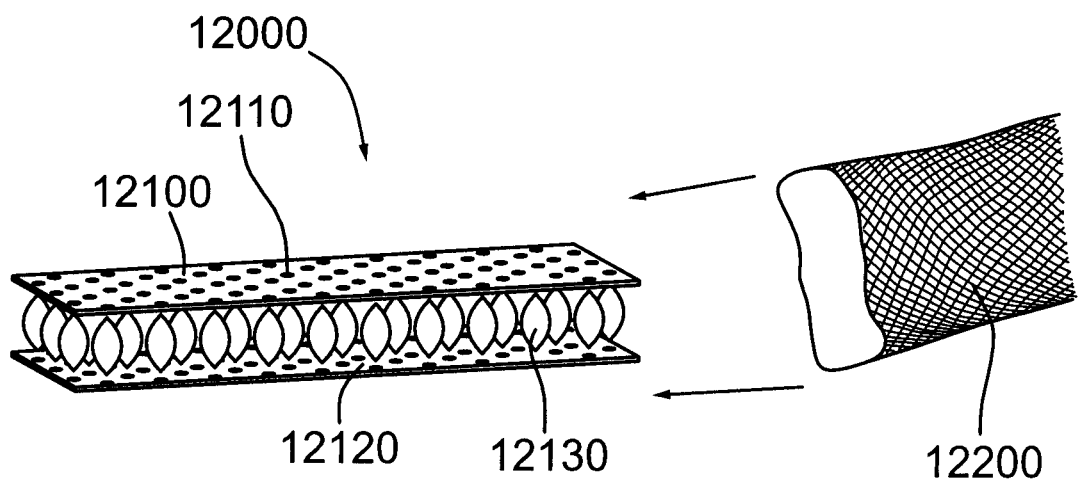
FIG. 12 is a first perspective view of a venting material being inserted into a tubinette to form a venting strip, according to an embodiment.
Figure 13:
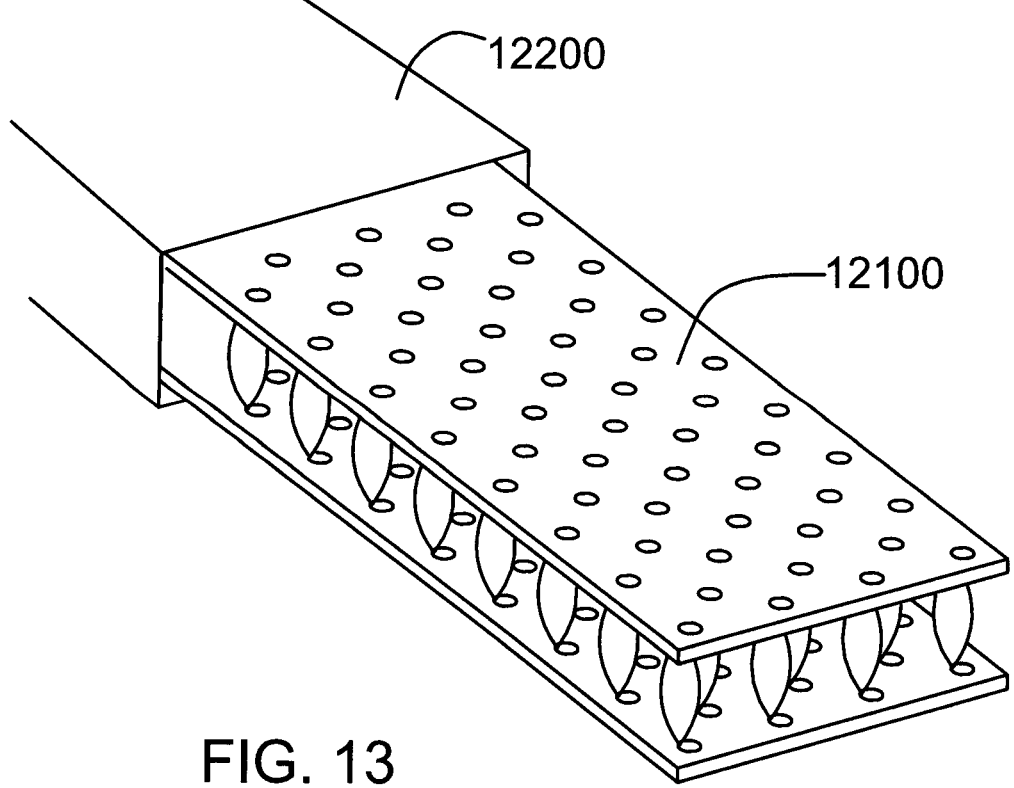
FIG. 13 is a second perspective view of the venting material and tubinette of FIG. 12.
Figure 14:
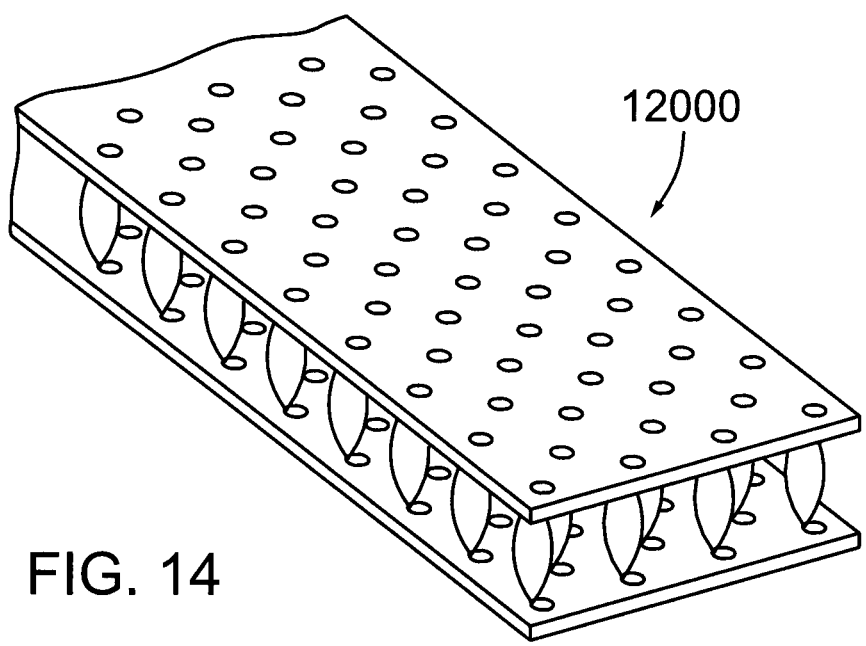
FIG. 14 is a perspective view of the venting material and tubinette of FIG. 12 forming the venting strip.

FIGS. 12 to 14 depict a venting strip 12000. Venting strip 12000 includes a strip of fabric-spacer material 12100 covered by a fabric tubinette 12200. Fabric-spacer material 12100 includes an upper layer 12110, a lower layer 12120, and a threads layer 12130. Upper and lower layers 12110 and 12120 are porous to allow for free air movement. Similarly, tubinette 12200 is porous, for example tubinette 12200 may be a netting or loose fabric. As depicted in FIGS. 13 and 14, fabric material 12100 is inserted inside tubinette 12200 to form a venting strip 12000.

Figure 15:
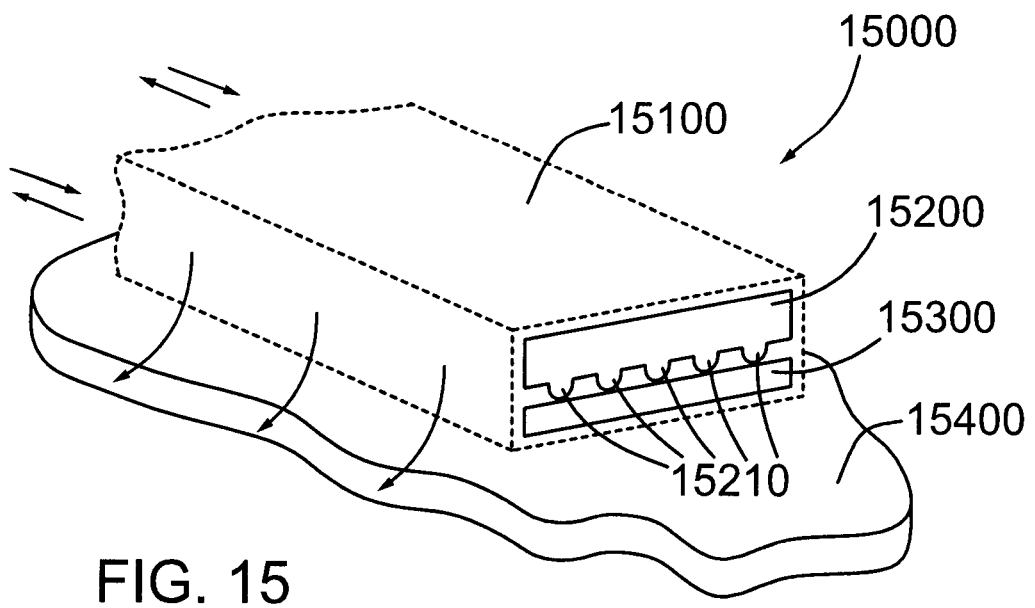
FIG. 15 is a perspective view of a venting strip, according to an embodiment, resting on a skin surface.
Figure 16:
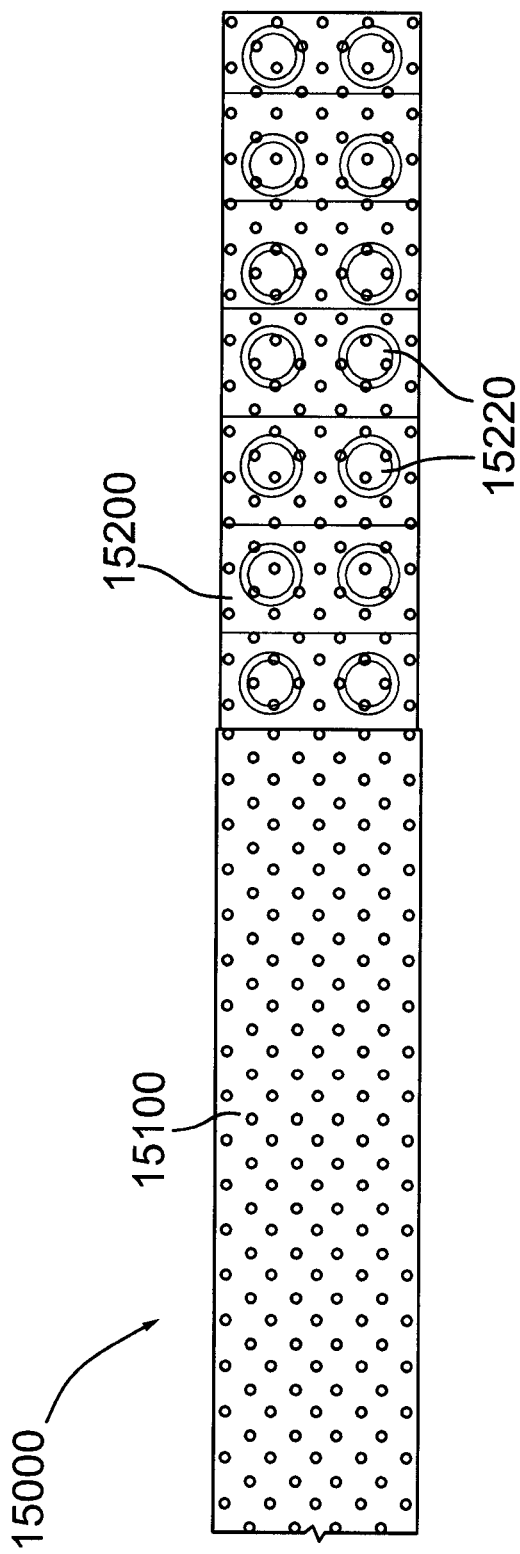
FIG. 16 is a bottom plan partial cut-away view of a venting strip, according to an embodiment.
Figure 17:
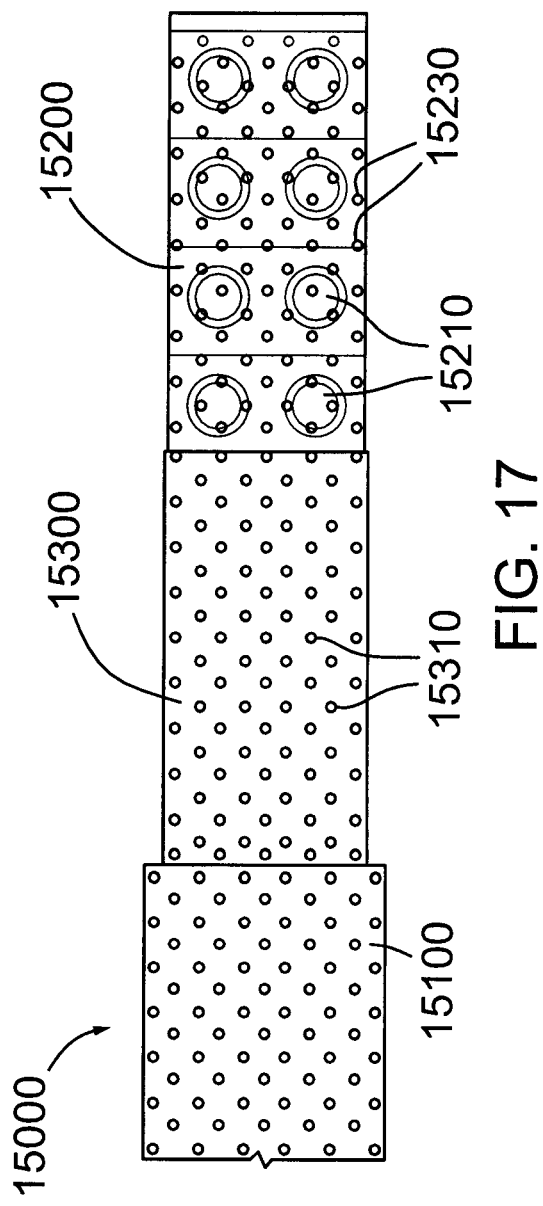
FIG. 17 is a top plan partial cut-away view of the venting strip of FIG. 16.

FIGS. 15 to 17 depicts a venting strip formed without fabric-spacer material. Venting strip 15000 includes an outer tubinette 15100 inside which is a venting sandwich. The venting sandwich is formed of a protrusion layer 15200 and a base layer 15300. The protrusion layer 15200 includes a set of protrusions 15210 directed towards the base layer 15300. Opposite the protrusions are a set of cavities 15220, and protrusion layer 15200 and base layer 15300 each define a set of apertures therethrough, 15230 and 15310 respectively, to allow freer flow of air. As depicted, venting strip 1500 is placed adjected a layer of skin 15400 and defines a venting space adjacent the skin 15400, the venting space defined between protrusion layer 15200 and base layer 15300. As shown particularly in FIG. 17, protrusions 15210 are separated by channels, lengthwise and widthwise channels. Channels also assist in increasing the flexibility of venting strip 15000.

Figure 18:
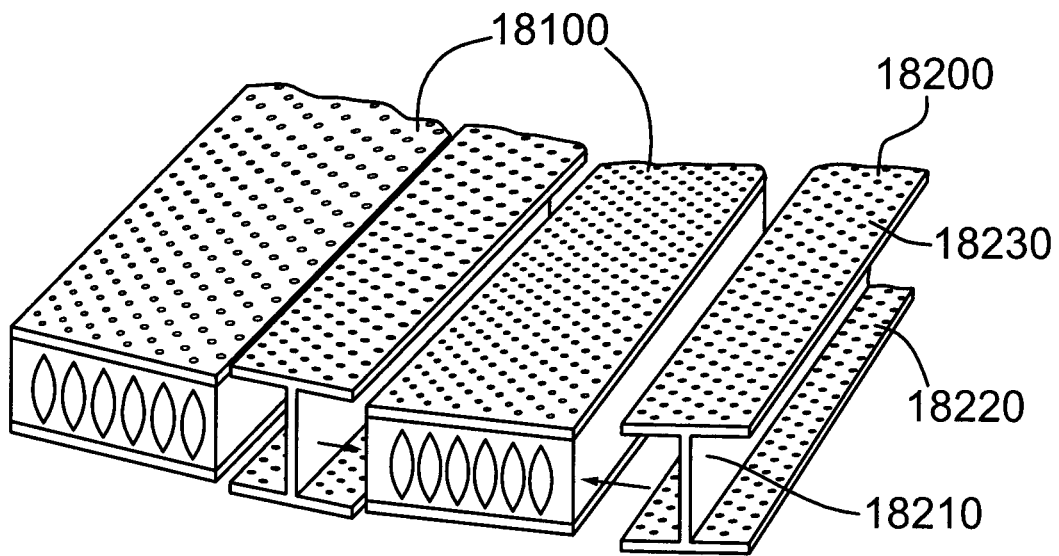
FIG. 18 are first and second perspective views of a set of venting strips and a set of buffers being brought together to form a venting device, according to an embodiment.
Figure 18:
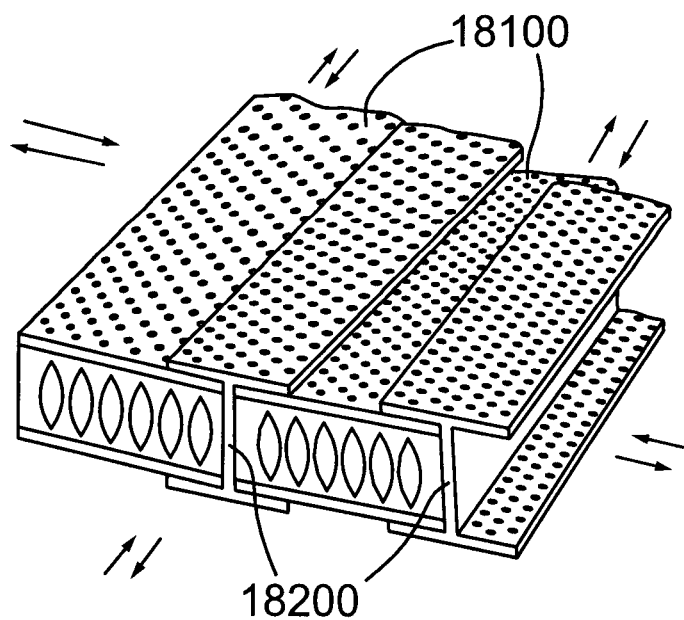
Figure 19:
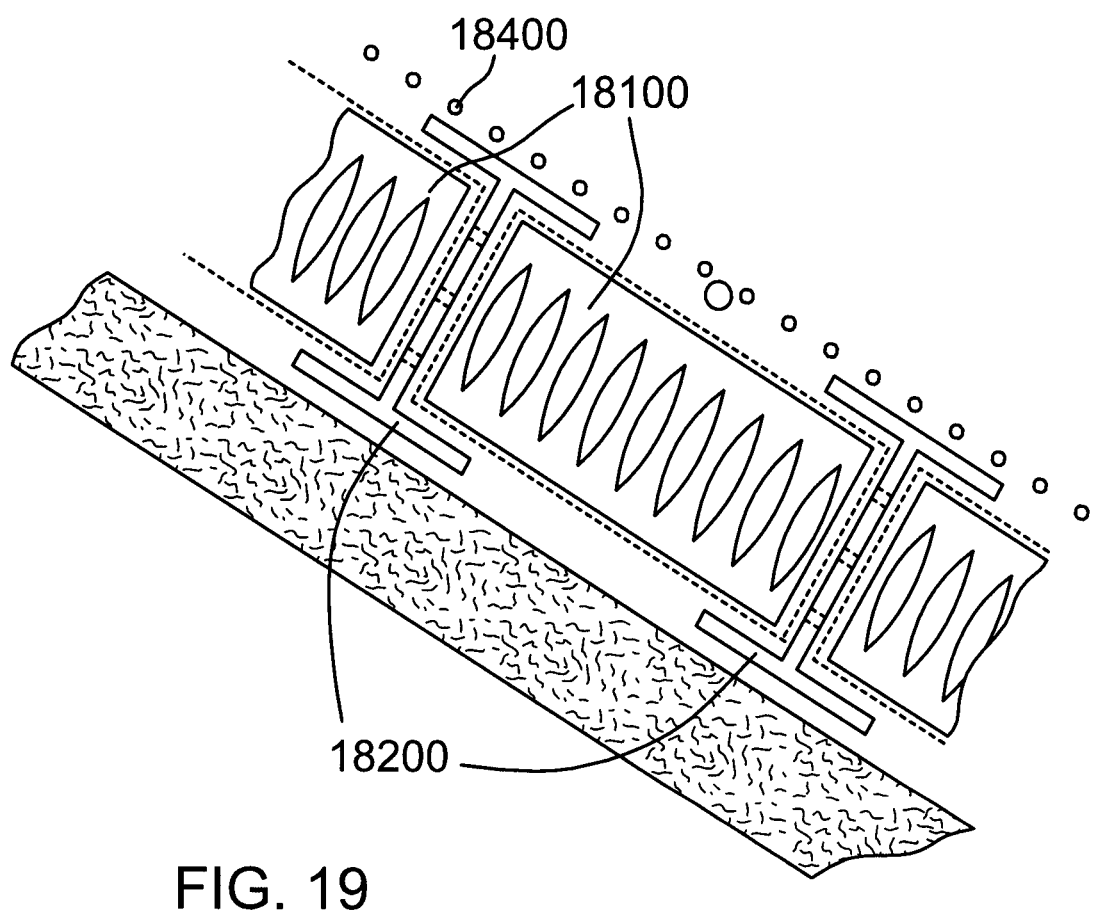
FIG. 19 is a cross sectional view of the venting device of FIG. 18, resting on a skin surface.
Figure 20:
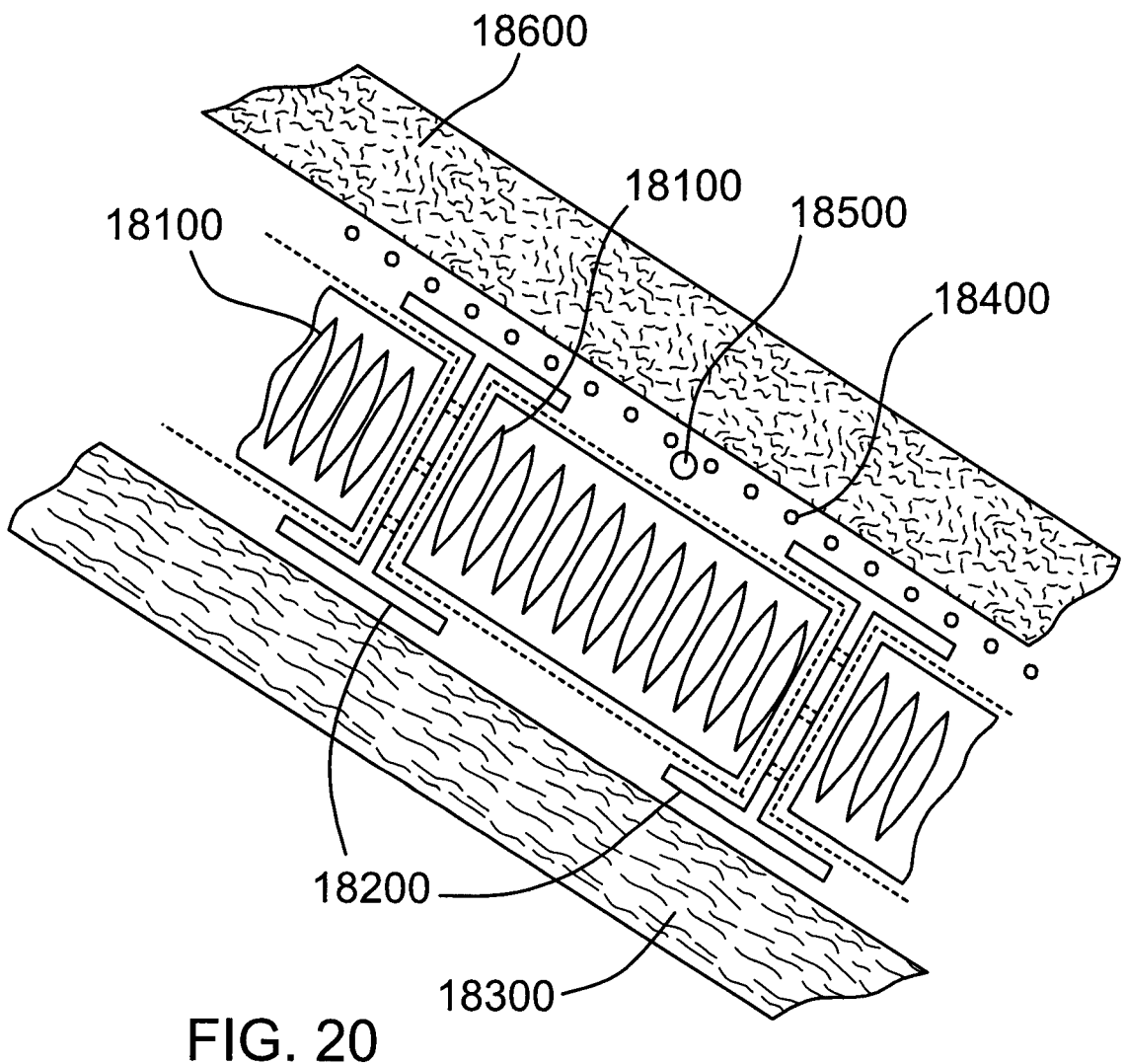
FIG. 20 is a cross sectional view of the venting device of FIG. 18, resting on a skin surface under a cast.

In forming venting devices, venting strips are brought together, separated by buffers. An embodiment is shown in FIGS. 18 to 20. Venting strips 18100 are each formed of a tubinette 18110 around a strip of fabric-spacer material 18120. Buffers 18200 each include a separation panel 18210 for separating adjacent venting strips, a shielding panel 18220 for shielding a user's skin 18300 from being caught between venting strips, and a securing panel 18230 for use in securing the buffer to an outer covering 18400 of a venting device. As depicted particularly in FIG. 20, tubinettes 18110 are secured to outer covering 18400 via stitches 18500 holding a thread of the tubinette to a thread of the outer covering. The buffers are secured to the outer covering via pieces of double-sided adhesive tape (not shown) mounted on a covering-facing surface of the securing panel 18230 and adhered to outer covering 18400. As depicted in FIG. 20, a venting device formed of the venting strips 18100, the buffers 18200, and the outer covering 18400 may be used in venting skin 18300 covered by cast 18600 such as a fiberglass or plaster of Paris cast.

In some embodiments, stitching holding one component to another may be a single loop or knot of thread, such as a surgical threaded knot. In some embodiments, stitching holding one component to another may be a line of stitching in the usual manner. Similarly, when double-sided adhesive tape or other adhesive is used, in some embodiments the adhesive is a single piece of adhesive while in some embodiments it is a strip or large patch of adhesive. Where intermittent anchoring points are used, in some embodiments each anchoring point is separated by intervals of approximately 3 to 6 cm in a string of anchoring points along the length of a venting strip or buffer. In some embodiments, where adhesive is used the adhesive anchor points may be 3 to 5 cm apart, and where thread is used the thread anchor points may be 4 to 6 cm apart. In some embodiments, an adhesive to be used is an ultraviolet-curable adhesive.

Figure 21:
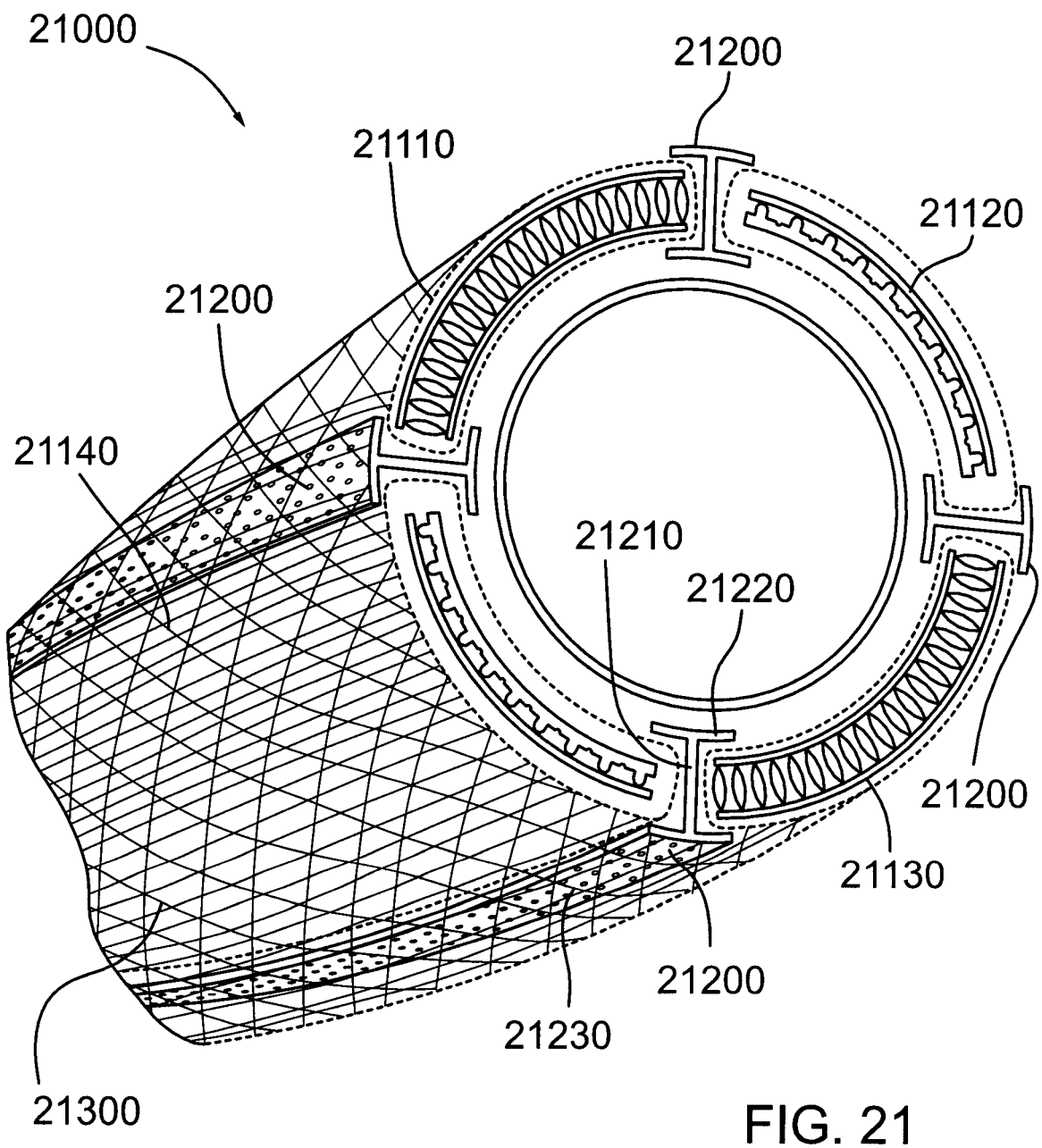
FIG. 21 is a perspective view of a venting device, according to an embodiment.
Figure 22:
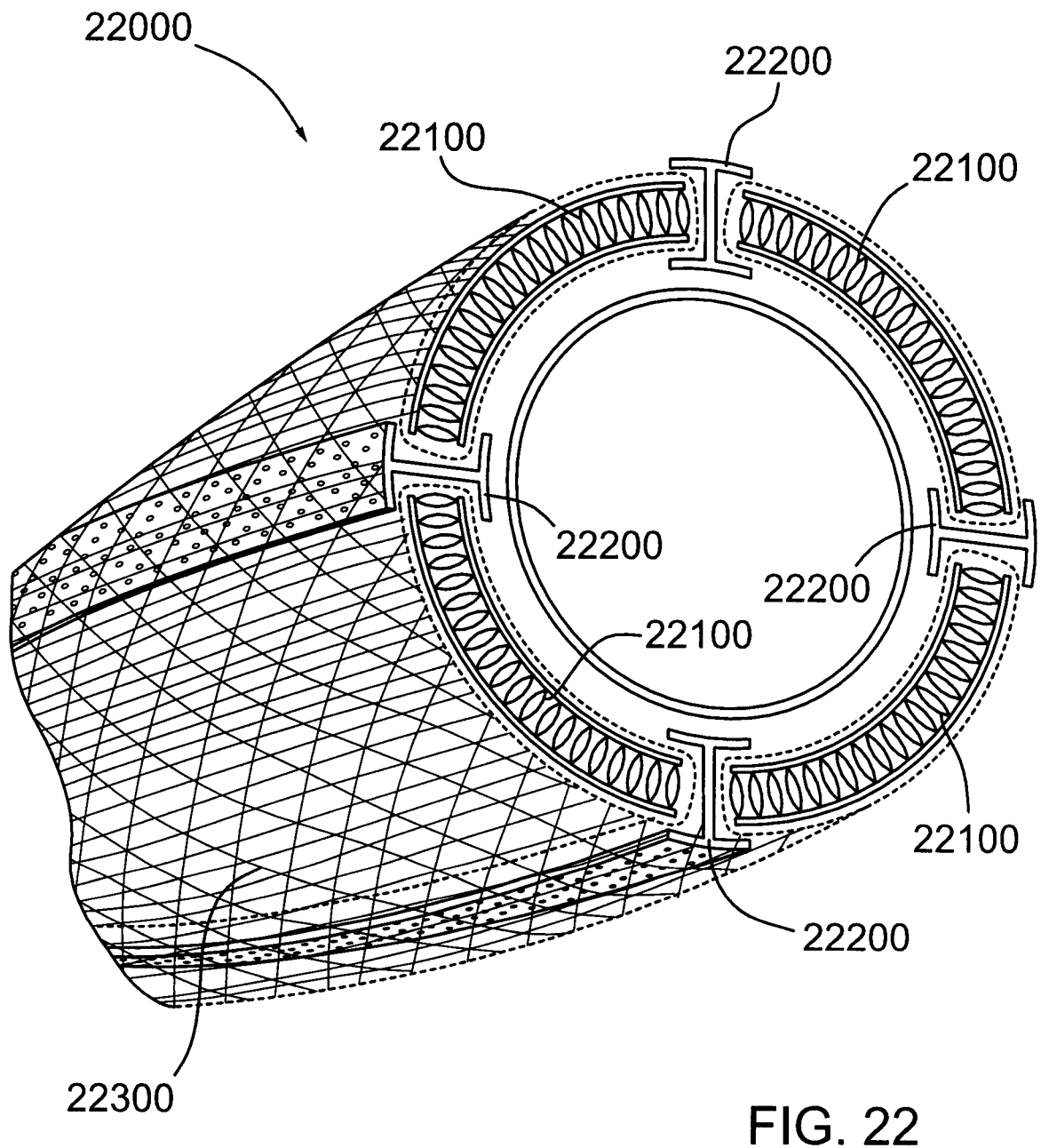
FIG. 22 is a perspective view of a venting device, according to an embodiment.
Figure 23:
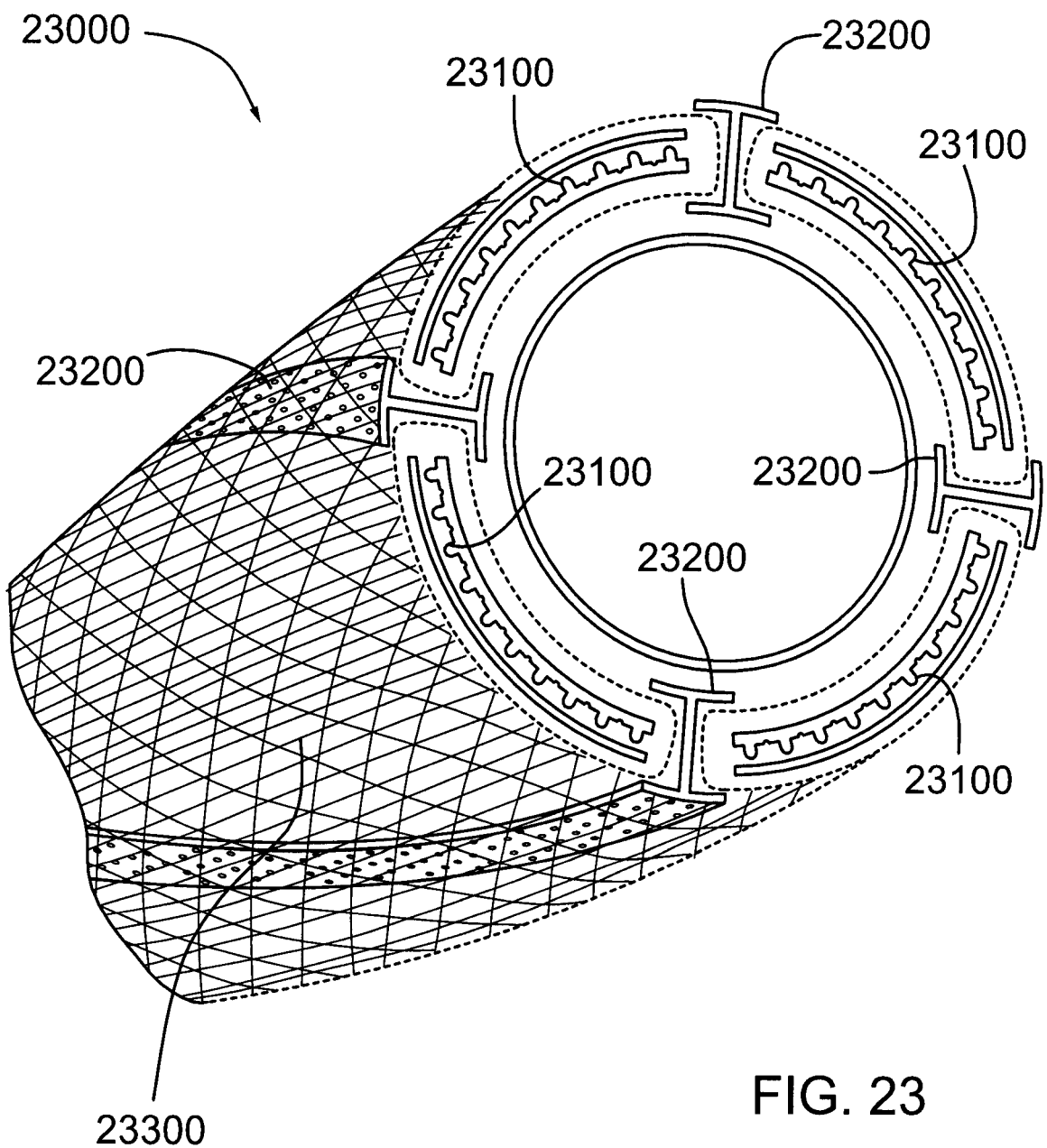
FIG. 23 is a perspective view of a venting device, according to an embodiment.

FIGS. 21 to 23 depict three embodiments of venting devices. Venting device 21000 includes a first venting strip 21110, a second venting strip 21120, a third venting strip 21130, and a fourth venting strip 21140. Each venting strip is spaced from adjacent venting strips by a shielding buffer provided to keep the tubular layer from pinching the skin of a user. Buffers 21200 are 'H' shaped channels which each include a barrier panel 21210 a shielding panel 21220 and a securement panel 21230. Venting device 21000 also includes an outer netting 21300. Outer netting 21300 is provided to hold the components of venting device 21000. For example, double-sided tape may be applied to the upper surface of each securement panel 21230 to interface with threads of outer netting 21300 to hold each buffer 21200 to outer netting 21300, and the tubinettes of the venting strips may be stitched to the outer netting 21300.

In venting device 21000 the venting strips are a combination of fabric-spacer strips and protrusion sandwich strips. Venting strips 21110 and 21130 are fabric-spacer strips, while venting device 21120 and 21140 are protrusion sandwich strips.

While venting device 21000 uses a mix of fabric-spacer strips and protrusion sandwich strips, in some embodiments all venting strips are fabric-spacer strips, and in some embodiments all venting devices are protrusion sandwich strips.

Venting device 22000 is an example of a venting device in which all venting strips 22100 are fabric-spacer strips, separated by buffers 22200 and held by netting 22300. Venting device 23000 is an example of a venting device in which all venting strips 23100 are protrusion sandwich strips, separated by buffers 23200 and held by netting 23300.

Figure 24:
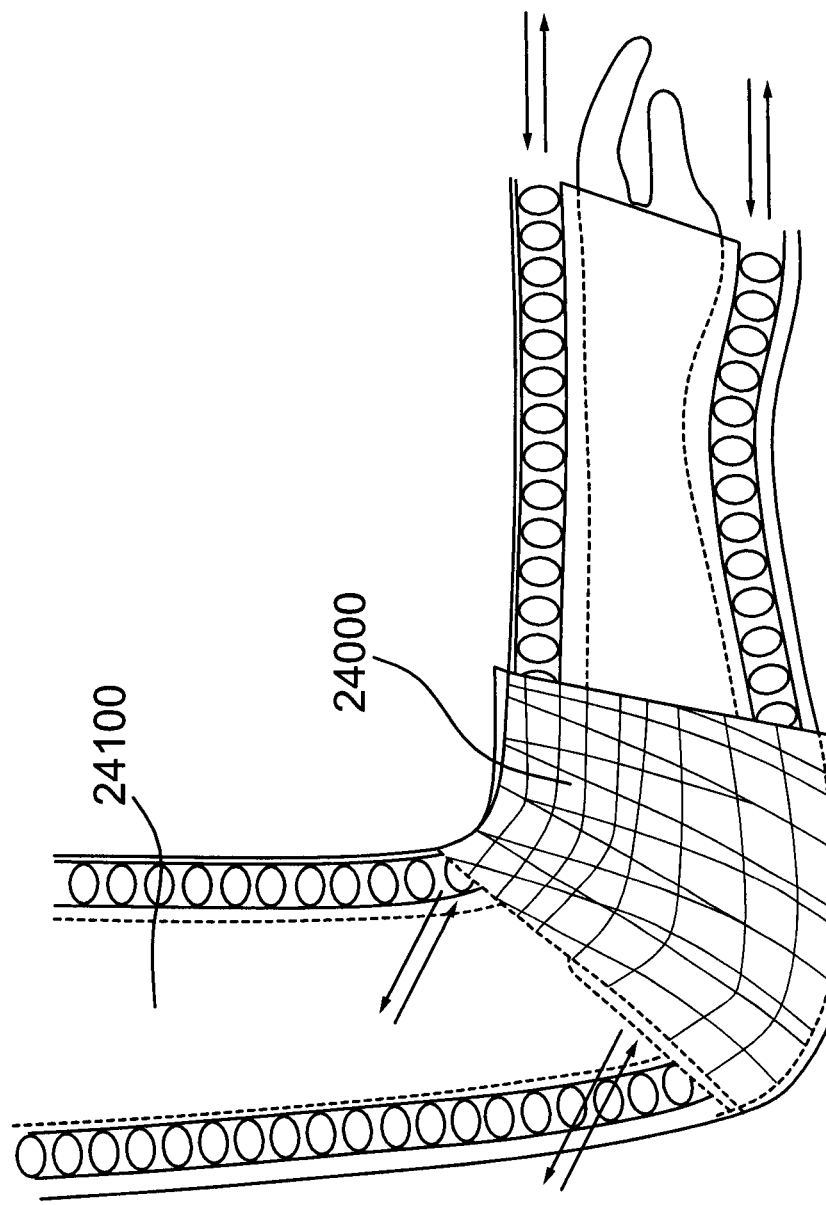
FIG. 24 is a side partial-cutaway view of a venting device, according to an embodiment, mounted on an arm.
Figure 25:
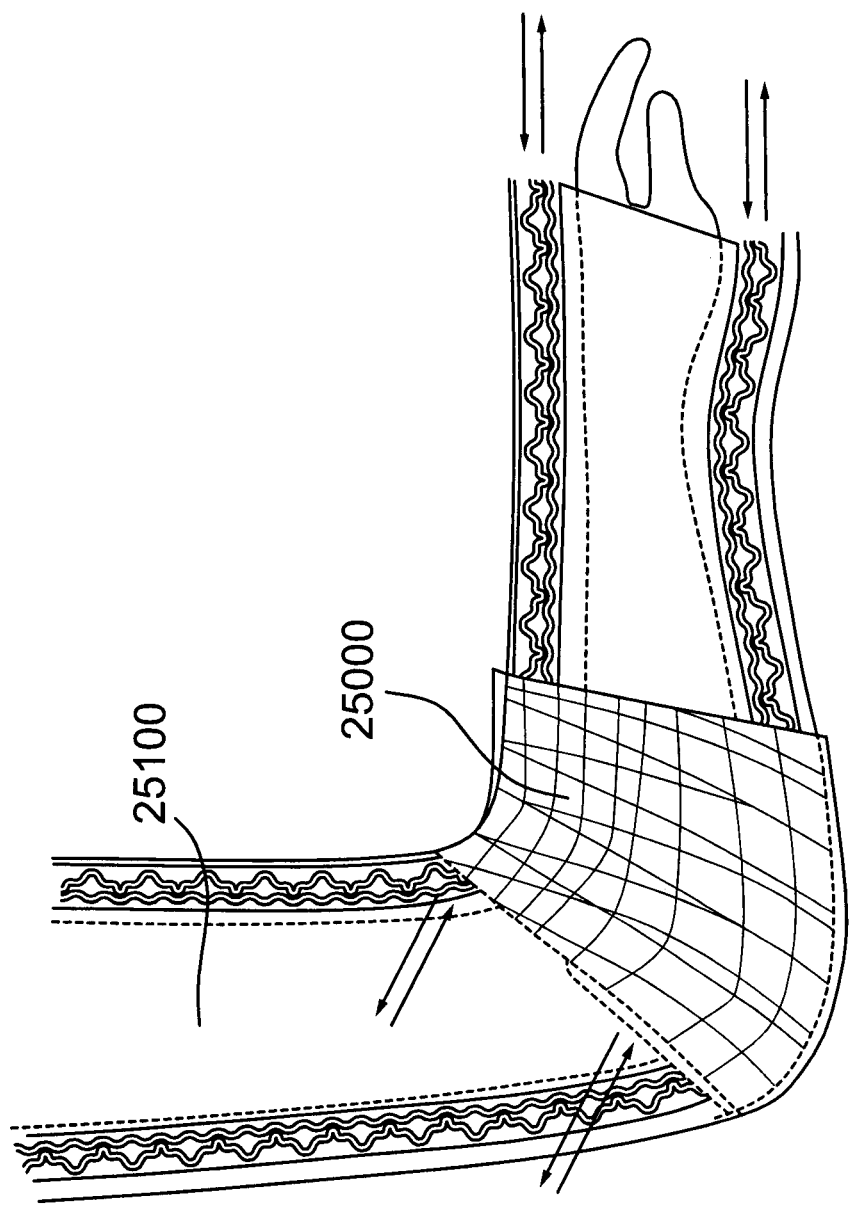
FIG. 25 is a side partial-cutaway view of a venting device, according to an embodiment, mounted on an arm.

As depicted in FIGS. 24 and 25, venting devices may be mounted on a limb or other vented subject. In FIGS. 24 and 25 venting devices 24000 and 25000 are mounted on arms 24100 and 25100, respectively. Venting devices 24000 and 25000 allow air to pass through to interface with the skin of the underlying arms.

Figure 26:
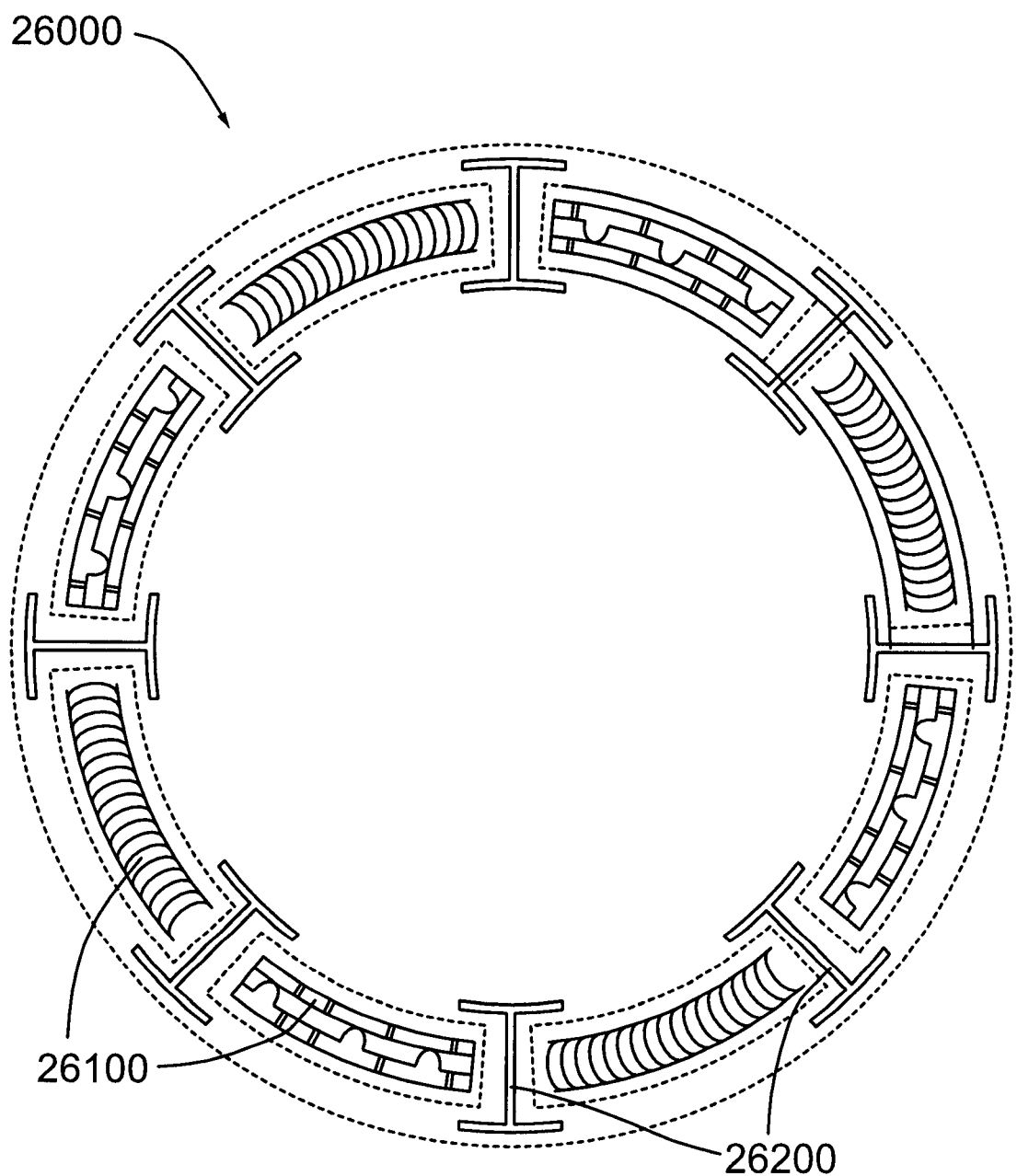
FIG. 26 is a first cross-sectional view of a venting device, according to an embodiment.

While venting devices 21000, 22000, and 23000 each includes four venting strips and four buffers, in other embodiments other numbers of buffers and stirps may be used. The number of buffers and strips to be used depends on the anticipated flexibility needs, the size of the venting device, and other factors. For example, Venting device 26000 of FIGS. 26 and 27 includes eight venting strips 26100 and eight buffers 26200. Venting device 26000 again includes a mix of fabric-spacer strips and protrusion sandwich strips. Although the fabric-spacer strips and protrusion sandwich strips alternate in venting device 26000, any mix may be used.

Figure 27:
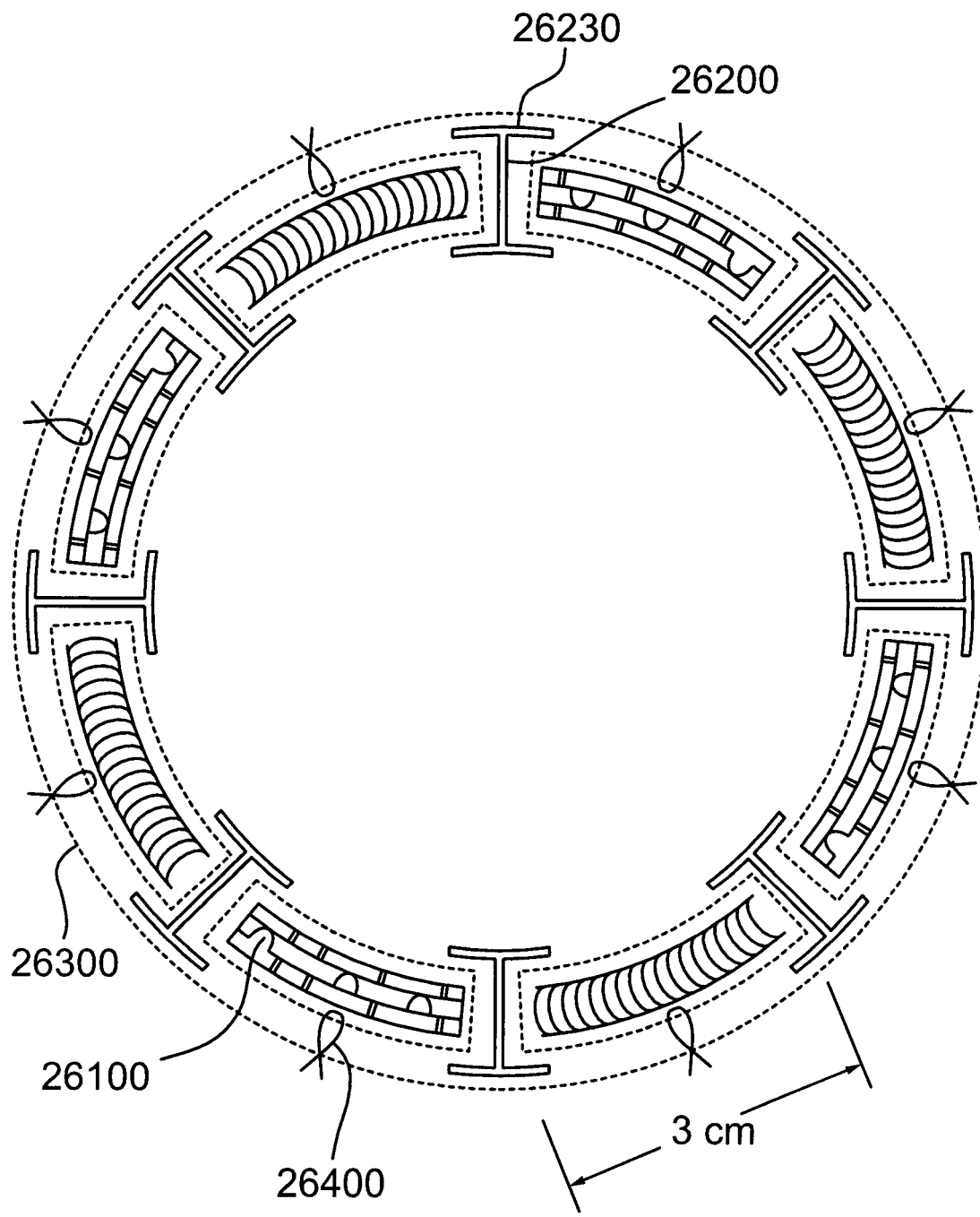
FIG. 27 is a second cross-sectional view of the venting device of FIG. 26.

As indicated in FIG. 27, tubinettes 26110 of venting strips 26100 are stitched to outer netting 26300 using thread loops 26400. Each venting strip is roughly 3 cm in width. Buffers 26200 are adhered to outer netting 26300 via double-sided adhesive strips (not shown) mounted on securement panel 26330 and interfacing with the portion of outer netting 26300 above each securement panel 26330.

Figure 28:
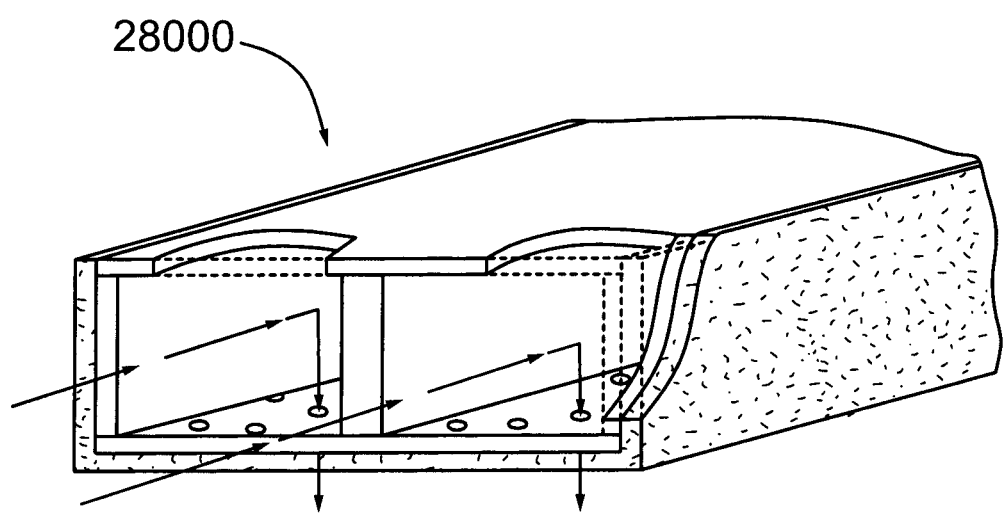
FIG. 28 is an isometric, schematic illustration of an example venting material, with portions broken away for purposes of illustration.
Figure 31:
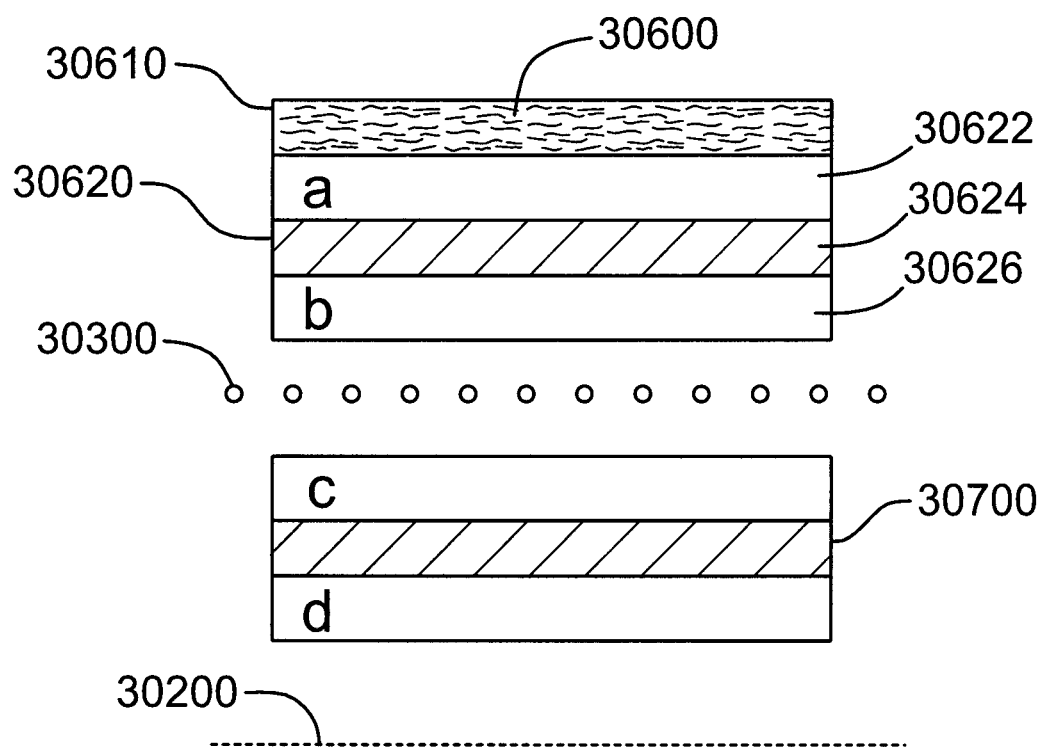
FIG. 31 is a cross sectional view of a decorative disc mounted on a venting device, according to an embodiment.

FIG. 28 depicts a simple venting material 28000 as was disclosed in U.S. Pat. No. 7,250,034 which is hereby incorporated in its entirety by reference. The venting material of FIG. 31 is an additional example of a venting material which may be used in forming venting strips for use in forming a venting device, in some embodiments.

Figure 29:
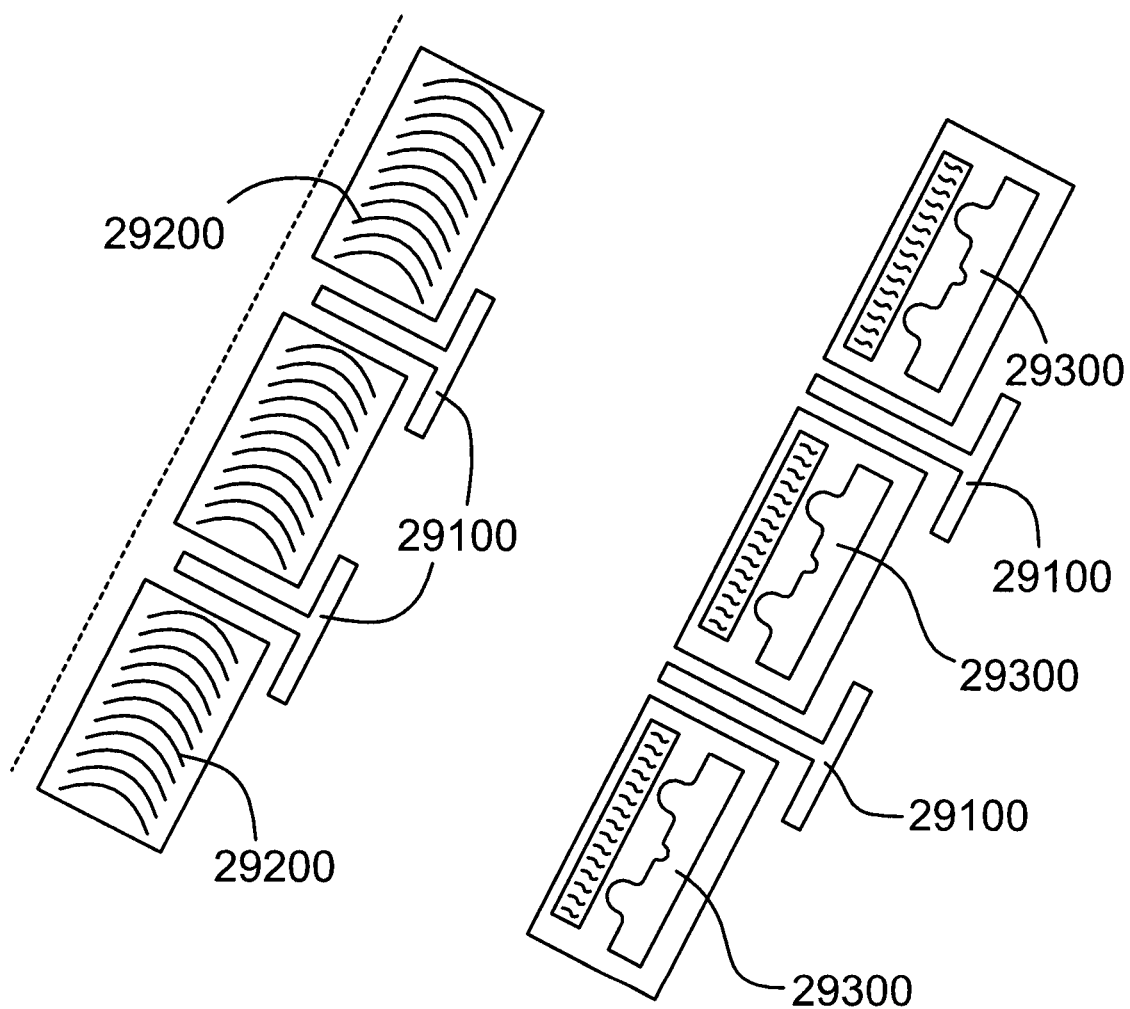
FIG. 29 is a cross-sectional view of a first venting device, according to an embodiment, and a cross-sectional view of a second venting device, according to an embodiment.

Buffers have thus far been depicted as 'H' shaped buffers, however in some embodiments other shapes may be used. For example, buffers 29100 of FIG. 29 are 'T' shaped buffers, which can be used with venting strips such as fabric-spacer strips 29200 or protrusion sandwich strips 29300. In some embodiments, a 'T' shaped buffer is used as venting device using the 'T' shaped buffer will face less mechanical stress because the 'T' buffers have less material than the 'H' buffers.

Figure 30:
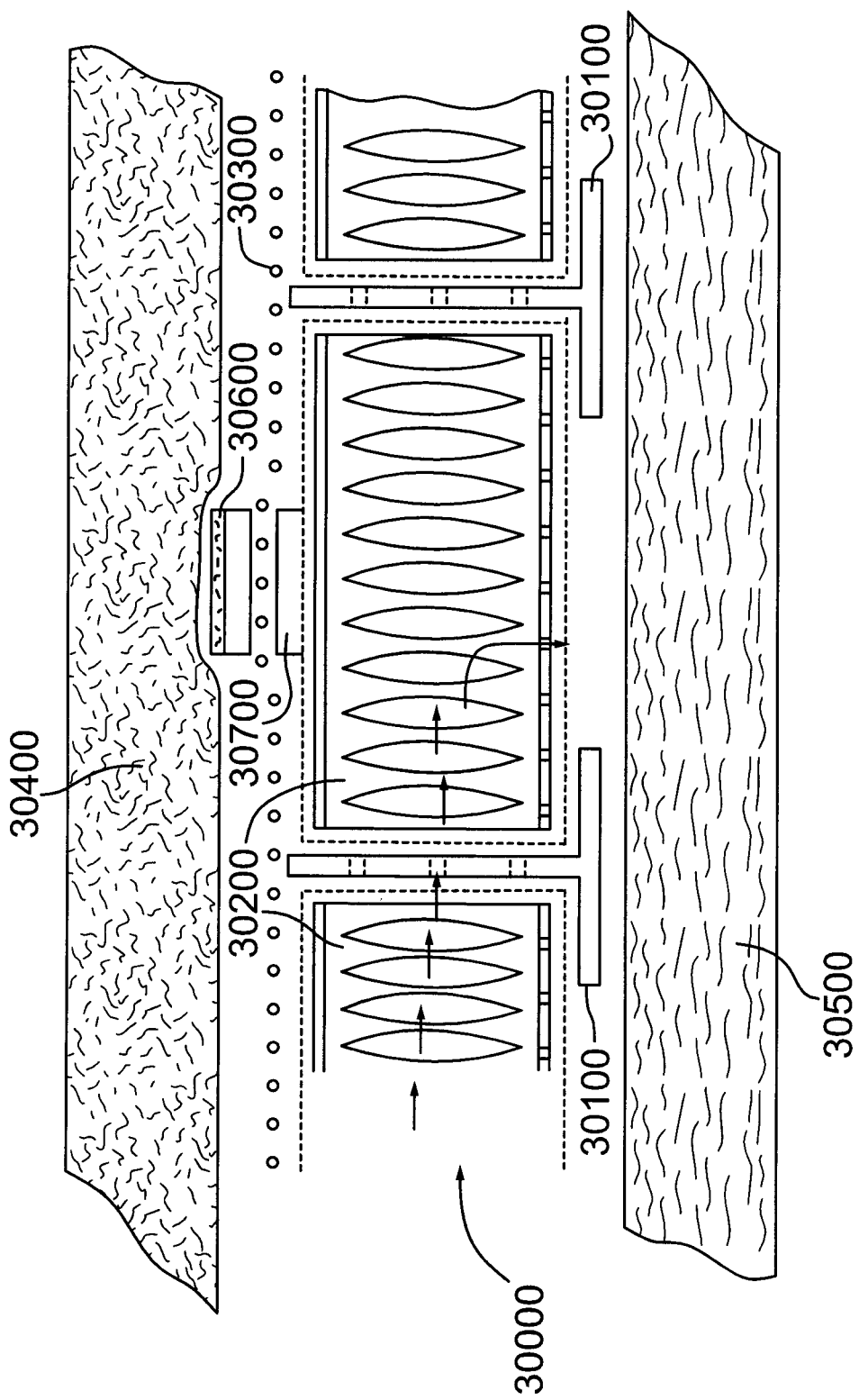
FIG. 30 is a cross-sectional view of a venting device, according to an embodiment, received between a cast and a skin surface.

An example of a venting device using 'T' shaped buffers is depicted in FIG. 30. Venting device 30000 includes a set of buffers 30100 separating a set of fabric-spacer strips 30200, the buffers 30100 and strips 30200 secured to an outer netting 30300. Venting device 30000 is placed between cast 30400 and skin 30500. Venting device 30000 includes a decorative disc 30600 adhered to outer netting 30300, decorative disc 30600 may be a logo or advertisement or set of instructions or warnings or other message. Each venting strip 30200 is secured to outer netting 30300 via a set of pieces of double-sided adhesive tape 30700. As indicated, buffers 30100 each includes a set of apertures to allow air to move through the buffer between venting strips. Buffers may also have apertures in the shielding panel to allow air to move interface with skin beneath the shielding panel.

Decorative disc 30600 is shown in greater detail in FIG. 30. Decorative disc 30600 has a decorative layer 30610 held by a double-sided adhesive layer 30620. Double-sided adhesive layer 30620 has a first adhesive layer 30622, a base layer 30624, and a opposite adhesive layer 30626. In some embodiments, double-sided adhesive tape segments are disc segments, such as 10 mm in diameter. In some embodiments a decorative disc is used which is 10 mm in diameter. A decorative disc may be made of paper, plastic, gel, silicone, polyurethane, cork, compressed cotton, foam, or any material which is hypoallergenic and can stand the sterilization processes.

Figure 32:
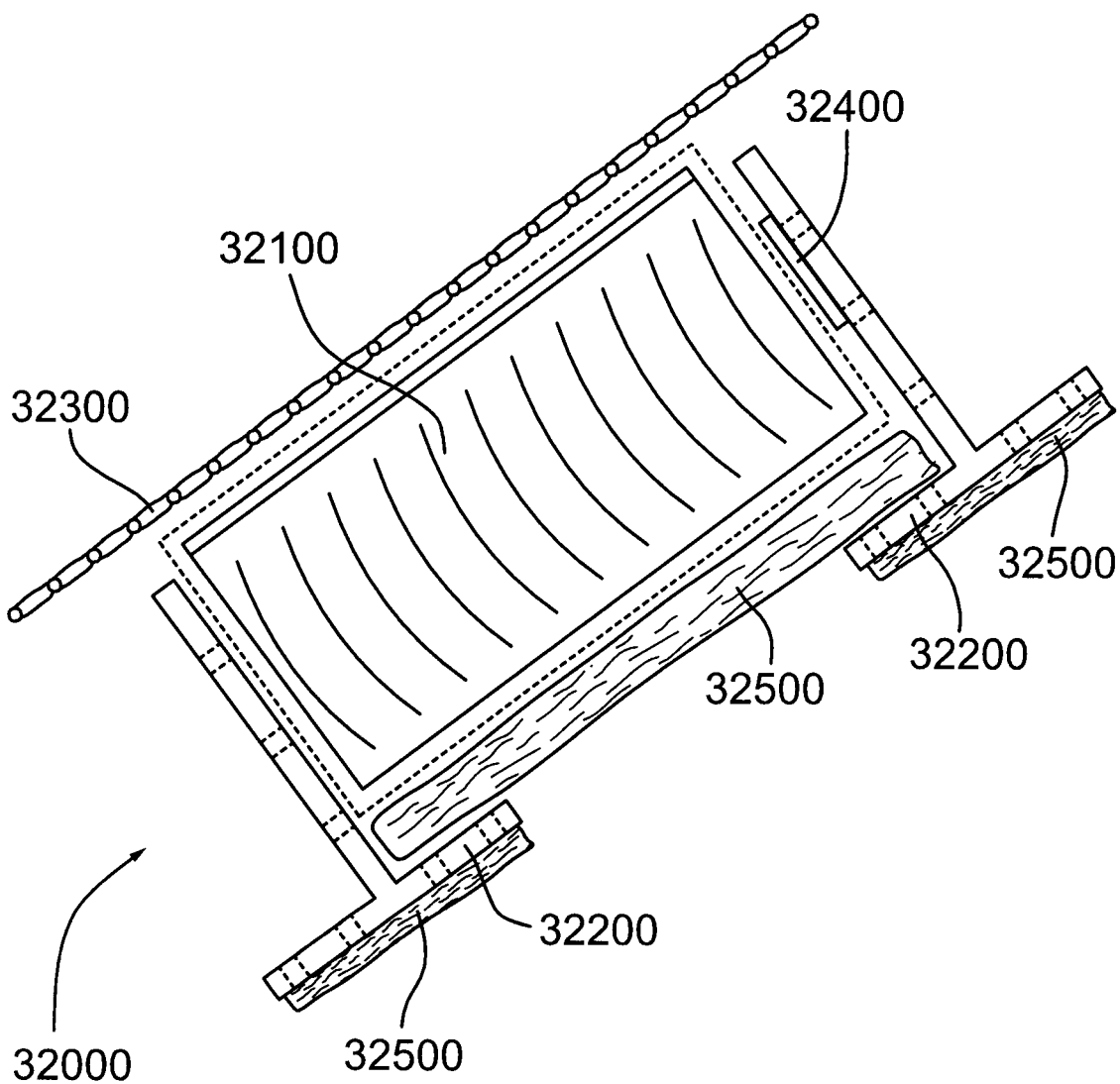
FIG. 32 is a cross-sectional view of a venting device, according to an embodiment.
Figure 33:
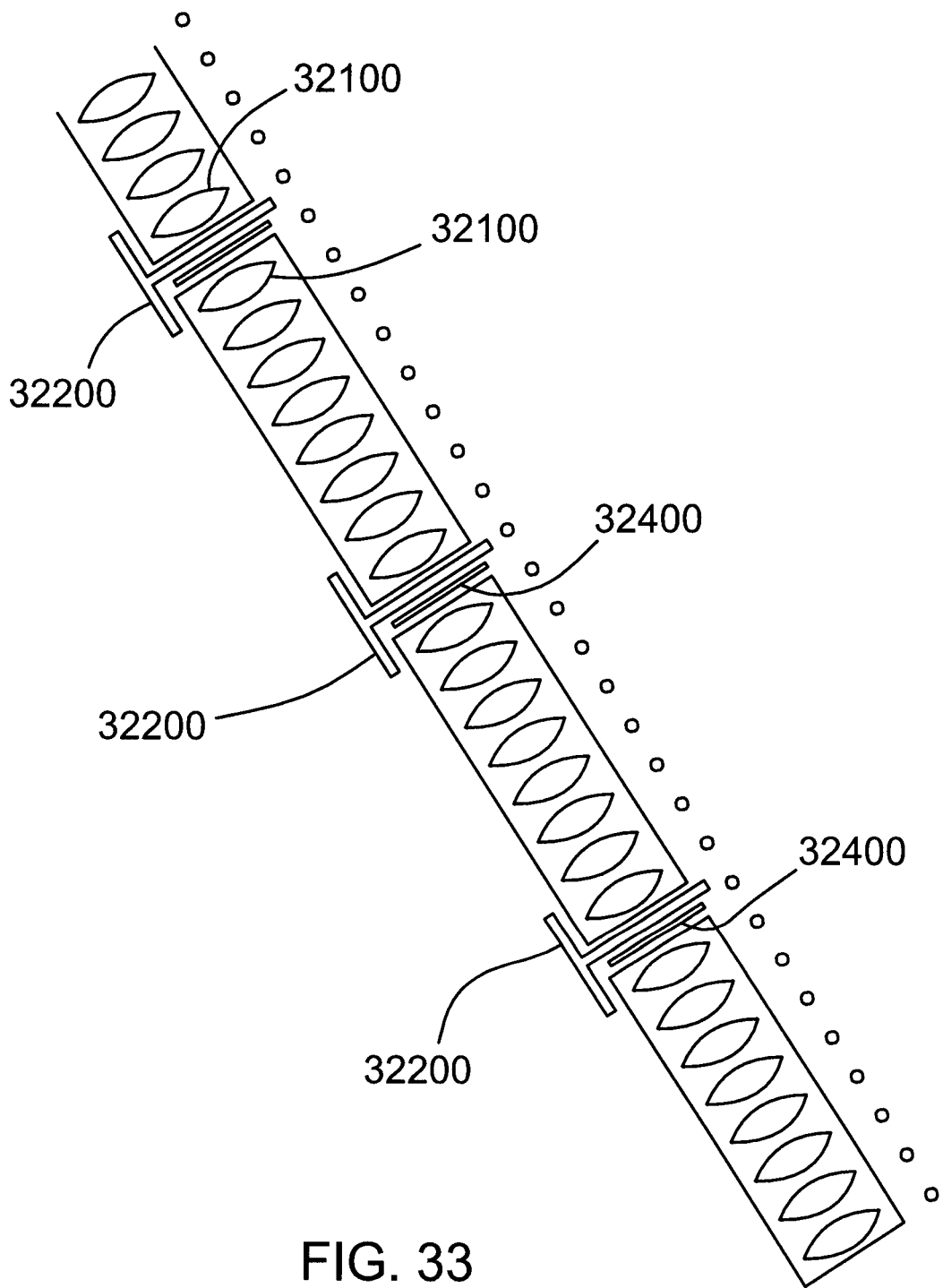
FIG. 33 is a cross-sectional view of the venting device of FIG. 32.

The use of 'T' shaped buffers rather than 'H' shaped buffers removes the securement panel which is used for mounting adhesive in securing the buffers to an outer netting. Buffers can be secured in to an outer netting a variety of ways without a securement panel. For example, FIGS. 32 and 33 depict venting device 32000. Venting device 32000 includes venting strips 32100, buffers 32200 and outer covering 32300. As before, venting strips 32100 are secured to outer covering 32300, such as by stitching or adhesive. However, in Venting device 32000, buffers 32200 are secured to venting strips 32100 instead of directly to outer covering 32300. Each buffer 32200 is secured to only one venting strip 32100, so that each pair of buffer and venting strip is free to move relative each adjacent pair of buffer and venting strip. Buffer 32200 is secured to venting strip 32100 via double-sided adhesive tape 32400.

As depicted in FIG. 32, venting device 32000 also includes additional cushioning 32500 between each buffer 32200 and each venting strip 32100. Cushioning is provided in some embodiments to assist in the comfort of the user, and is porous and air permeable. Cushioning may be, for example, cotton padding.

Figure 34:
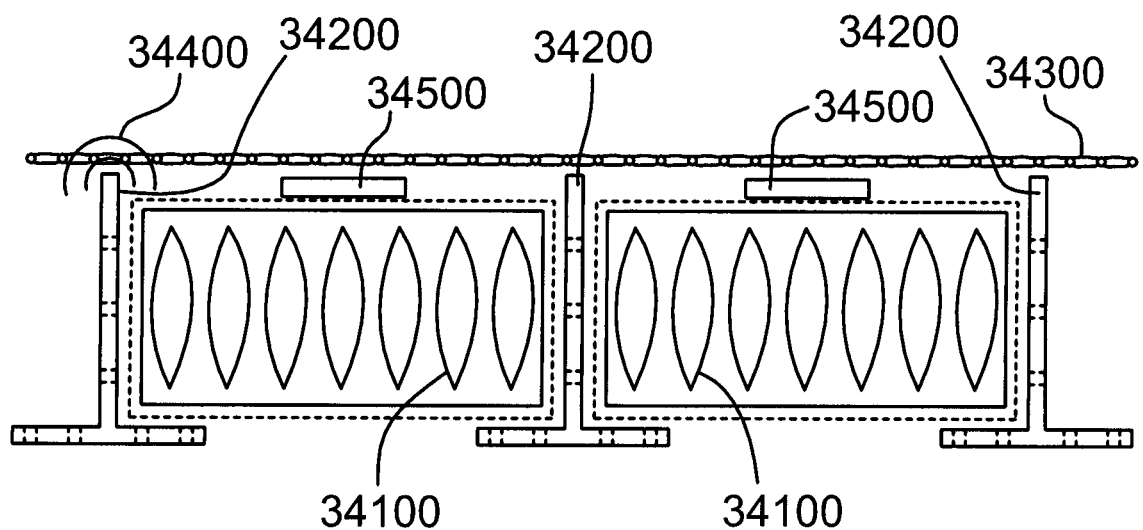
FIG. 34 is a cross-sectional view of a venting device, according to an embodiment.

However, securing buffers to venting strips is not the only option for securing 'T' shaped buffers. For example, venting device 34000 of FIG. 34 has buffers 34200 secured to netting 34300 via stitching 34400, and venting strips 34100 secured to netting 34300 via adhesive 34500.

Figure 35:
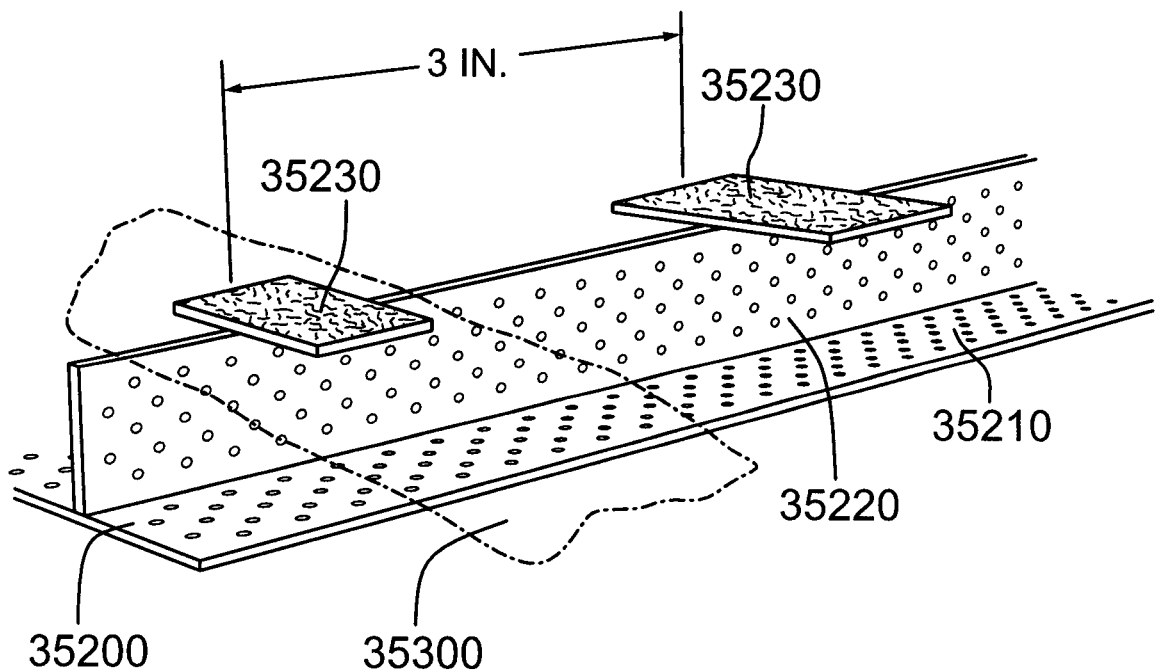
FIG. 35 is a perspective view of a buffer, according to an embodiment.
Figure 36:
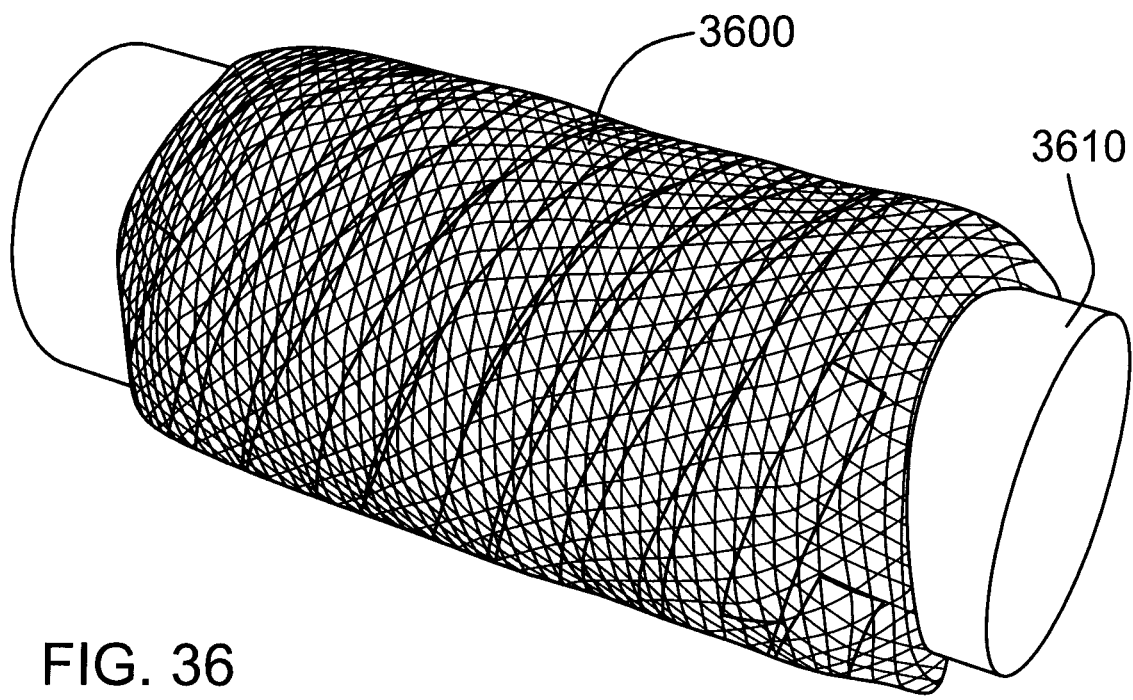
FIG. 36 is a perspective view of a venting device, according to an embodiment, mounted on a delivery tube.

In a further example, buffer 35200 of FIG. 35 has a separation panel 35210, a shielding panel 35220 and a set of mounting panels 35230. The set of mounting panels is a regularly-spaced set of panels attached to the separation panel opposite the shielding panel and provided to form mounting points for double sided adhesive to secure the buffer 35200 to netting 35300.

FIGS. 36 to 42 depict a method of mounting a venting device 36000 onto a user arm 37000.

Figure 37:
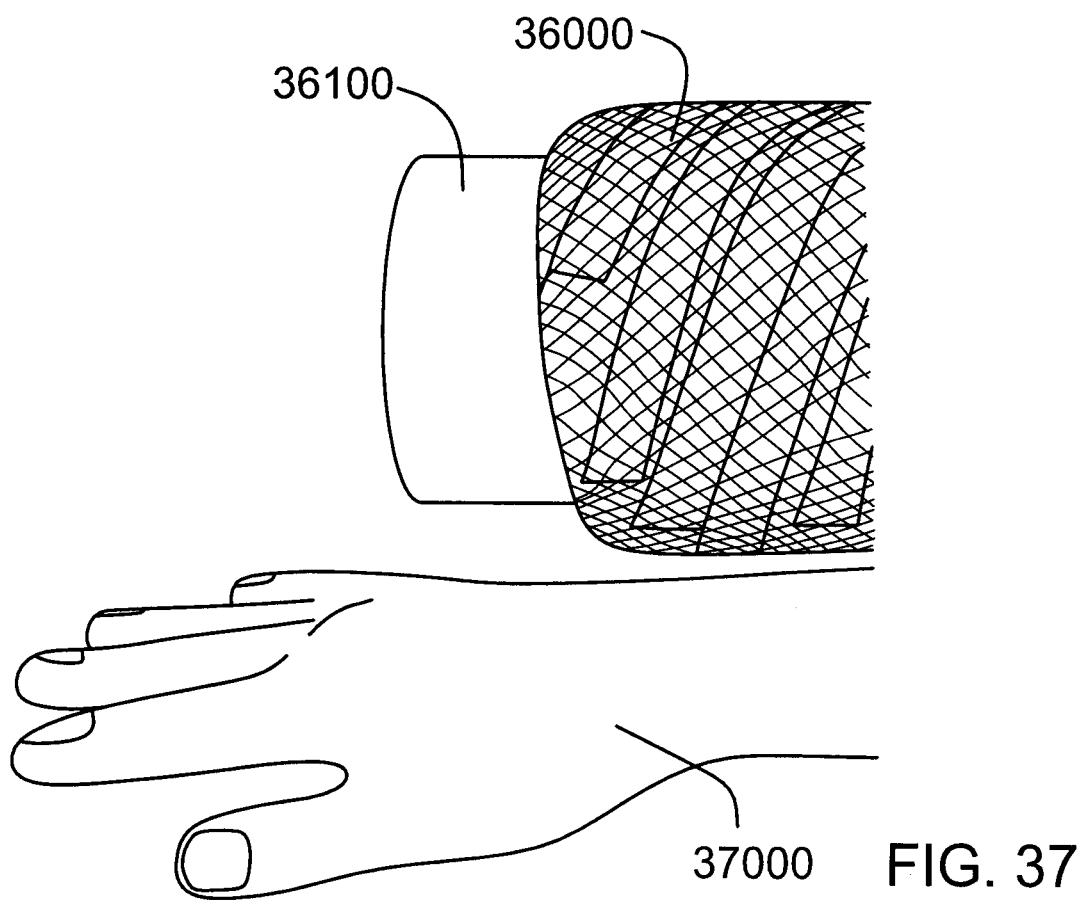
FIG. 37 is a perspective view of the venting device of FIG. 36, next to a vented subject.
Figure 38:
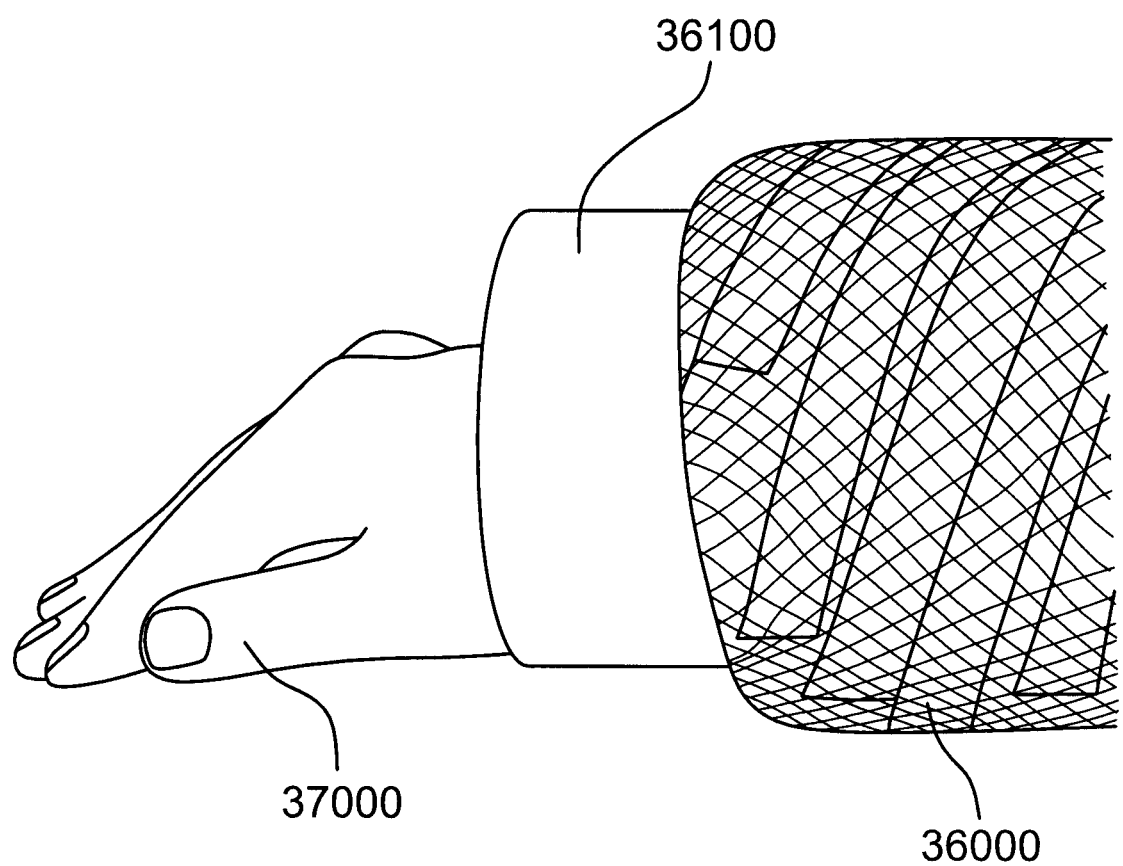
FIG. 38 is a perspective view of the vented subject of FIG. 37 inside the delivery tube of FIG. 36.

Venting device 3600 is formed of a set of venting strips and buffers secured to an outer netting, as described above. In the embodiment depicted in FIG. 36, venting device 36000 is mounted on a tube 36100 for delivery. As depicted in FIG. 37 a user chooses a venting device of roughly equivalent size to the limb on which it is to be mounted. Arm 37000 is compared to venting device 36000 to determine if an appropriate match is found. For example, as depicted in FIG. 38, if arm 37000 fits within delivery tube 36100, the venting device of this embodiment mounting method is determined to be appropriately sized.

Figure 39:
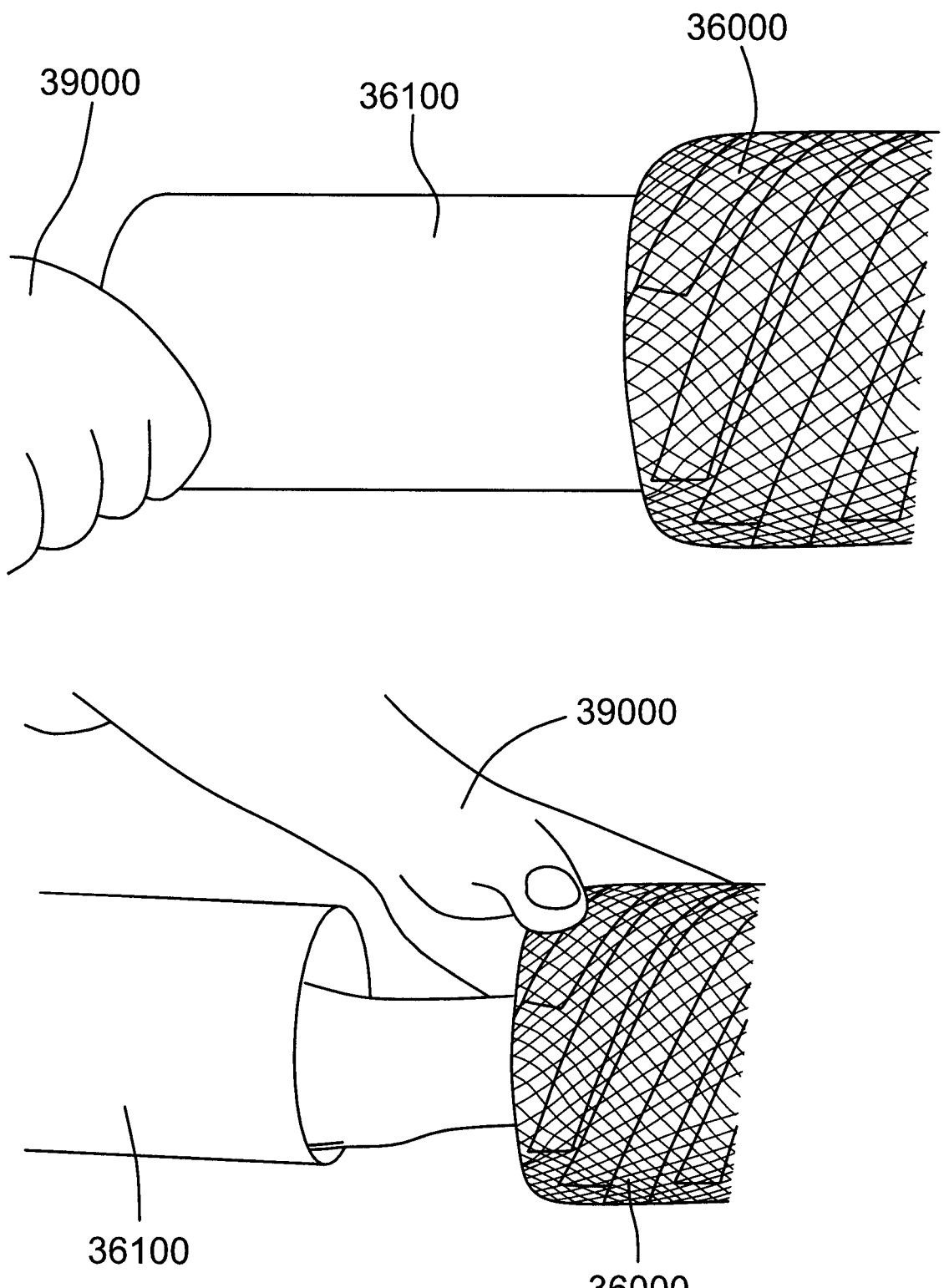
FIG. 39 are perspective views of the vented device of FIG. 36 being removed from the delivery tube and placed onto the vented subject of FIG. 37.
Figure 40:
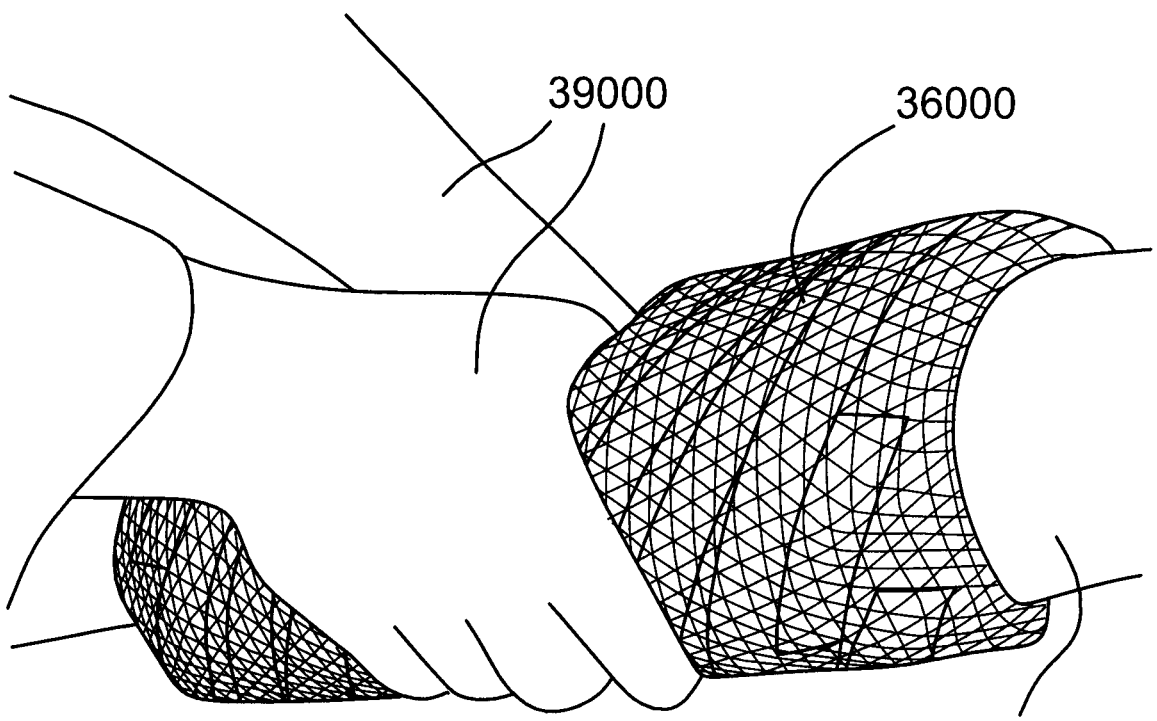
FIG. 40 is a perspective view of a supporting user reconfiguring the venting device of FIG. 36.
Figure 41:
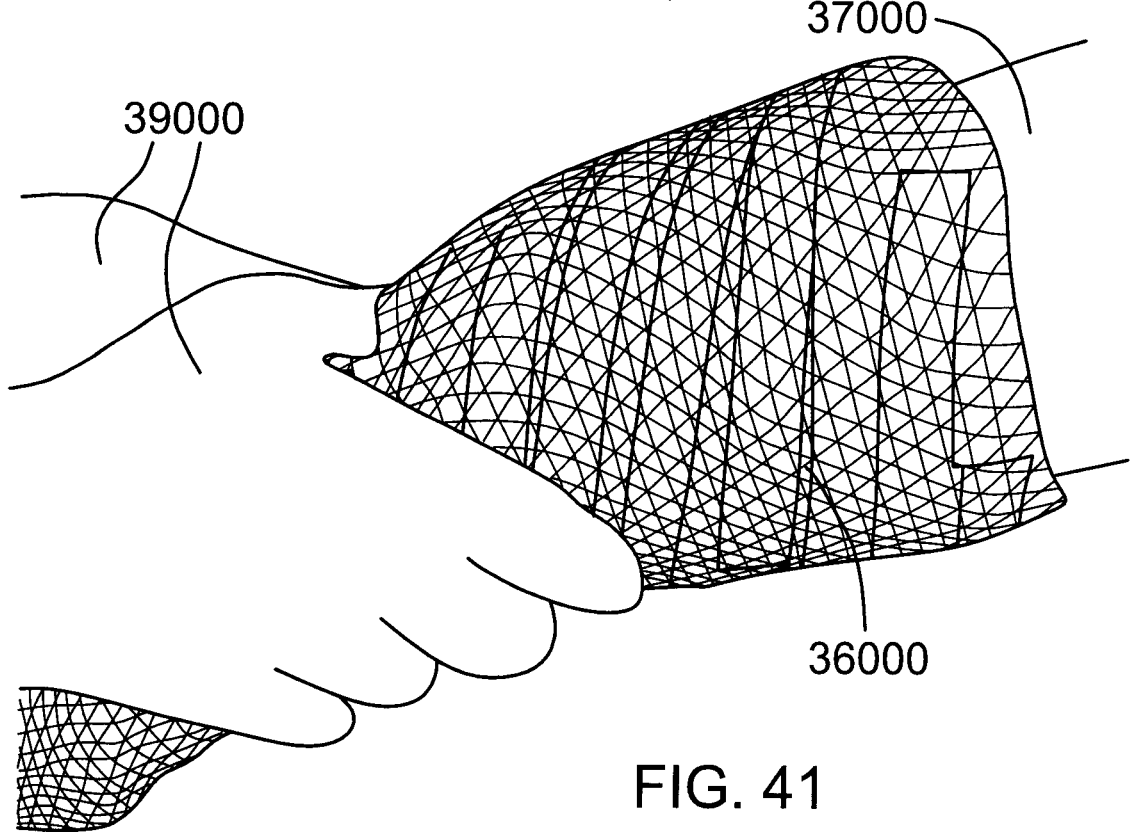
FIG. 41 is a perspective view of the supporting user of FIG. 39 further reconfiguring the venting device of FIG. 36.
Figure 42:
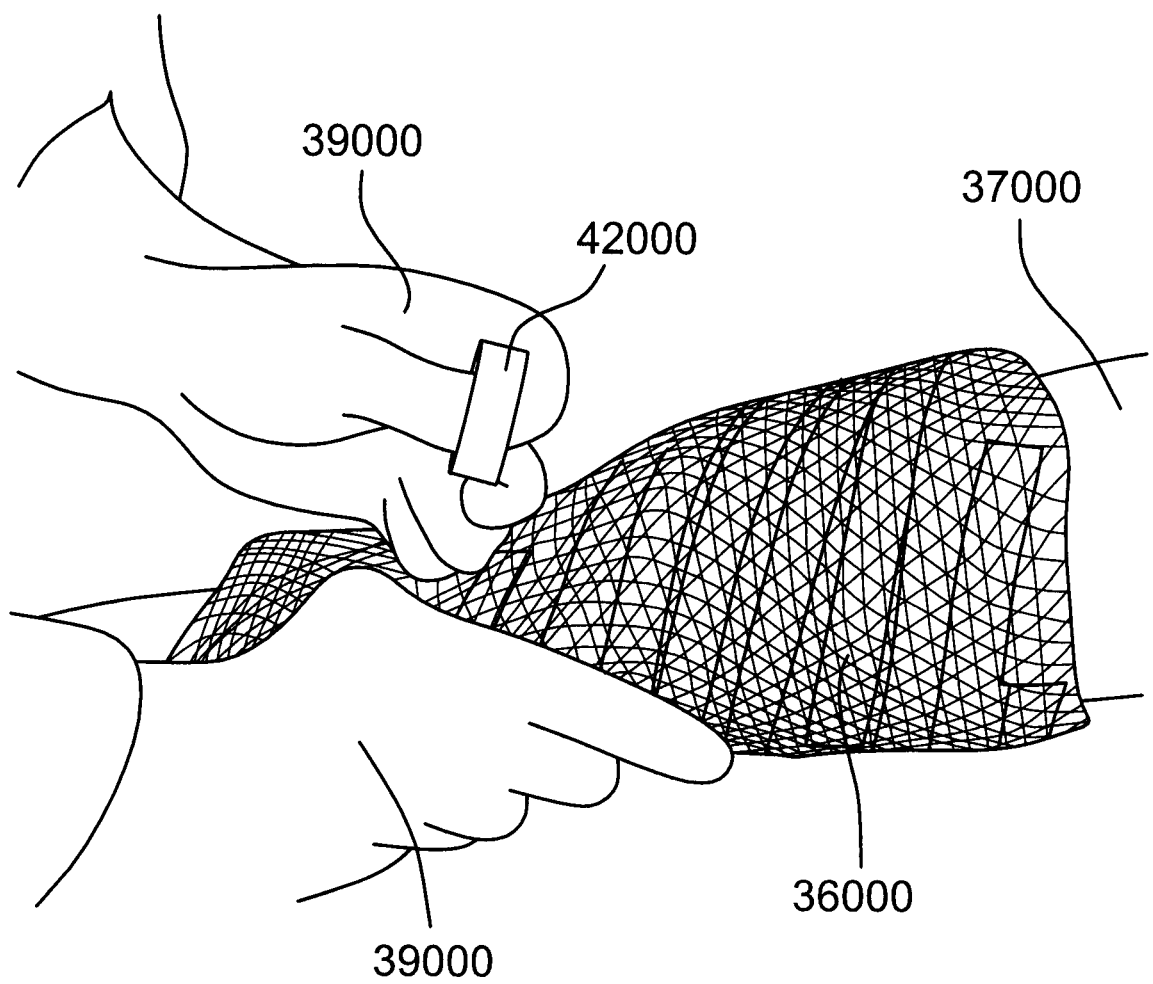
FIG. 42 is a perspective view of the supporting user of FIG. 39 securing the venting device of FIG. 36.

As depicted in FIG. 39, venting device 36000 is removed from delivery tube 36100 and inserted over arm 37000 by supporting user 39000. In some embodiments, a venting subject is inserted into a delivery tube and then the delivery tube is removed from under the venting device to leave the venting device in position around the venting subject. As depicted in FIGS. 40 to 42, supporting user 39000 then twists venting device 36000 to form venting device 36000 into a position which substantially matches the contours of arm 37000. Supporting user 39000 then secures the venting device to uncovered surfaces of arm 37000 using adhesive tape 42000, such as surgical tape.

Venting strips are arranged helicoidally in manufacturing to permit easier twisting. In some embodiments, the helicoidal arrangement is not pronounced.

In some embodiments, a venting device can also be used in compression therapy. For example, a venting device, or an element thereof such as an outer covering, may be sized smaller than a venting subject such as an arm so that the venting device applies a compressive force to the venting subject when mounted. In another example, the venting device itself may be larger than a venting subject, but may be formed into a size smaller than the venting subject by twisting the device.

Throughout this description specific embodiments have been described in which various elements are anchored to other elements via adhesive or stitching, however it is to be understood that other securing or anchoring elements may be used as well, such as hook-and-loop fasteners, buttons, magnets, ultraviolet adhesives, and other mechanical fasteners.

In some embodiments, a venting strip is made of a combination of fabric-spacer material and a protrusion sheet. For example, when a fiberglass cast is compressed to form it around a target surface, it may result in compression to a fabric-spacer material which may damage the ability of the fabric-spacer material to facilitate air flow, therefore a protrusion sheet may be incorporated into the fabric-spacer material to provide support for the fabric-spacer material and increase its resiliency. However, in some embodiments the buffers provide support, in some embodiments the use of a combination of fabric-spacer strips and protrusion strips provides the required resiliency, and in some embodiments the fabric-spacer material is inherently sufficiently resilient or is for use alone or with non-compressed devices.

Many of the embodiments of a venting device depicted and described have a tubular member having open first and second ends, however it is to be understood that in some embodiments a venting device may incorporate further extensions of venting material for particular uses. For example, a venting device for use with an arm cast may include a strap for use in passing between a user's thumb and the user's fingers in the form of a strap over the hand if the cast is expected to also incorporate such an extension.

In some embodiments, a venting device is sterilized and transported in a manner to maintain sterilization until use, such as sealed in plastic. In some embodiments, venting devices incorporate silver ions to limit the growth of bacteria. In some embodiments a venting device is medicated. For example, one or more components are coated with antimicrobial agents. For example, the buffers may be coated with antimicrobial agents.

In some embodiments, a venting device is between 1 and 20 mm thick. In some embodiments each venting strip is between 1 and 20 mm thick. In some embodiments, each fabric-spacer material is between 1 and 20 mm thick. In some embodiments each tubinette of a venting strip includes two or more layers of venting material, such as two layers of fabric-spacer material or two layers of protrusion material or a layer of fabric-spacer material and a layer of protrusion material. In some embodiments, in which a venting strip includes two or more layers of venting material, each of the layers of venting material can have an independently designed set of physical or chemical characteristics.

In some embodiments, a venting device is a venting sheet rather than a venting tube. In some embodiments a venting device is used also as a load absorption device for the comfort of a wearer. In some embodiments, all or substantially all elements of a venting device are perforated or include apertures, such as to allow air movement.

Various embodiments of the invention have been described in detail. Since changes in and or additions to the above-described best mode may be made without departing from the nature, spirit or scope of the invention, the invention is not to be limited to those details but only by the appended claims.

What is claimed is:

1. A venting device for wearing on a patient's limb, comprising:
a flexible outer covering having an outer surface and an inner surface, the outer covering having a first end and a second end and a longitudinal axis therebetween, wherein the outer covering is tubular such that the first and second ends are open;
a tubular assembly inside the outer covering and supported substantially coaxially thereof, wherein the tubular assembly has a diameter inside which the patient's limb is received, the tubular assembly comprising:
a set of venting strips arranged at angularly spaced positions to each other around the longitudinal axis to define seams between each adjacent pair of the venting strips, wherein the venting strips are anchored to the inner surface of the outer covering, wherein the venting strips extend axially and angularly in a common direction about the longitudinal axis to follow substantially parallel and helical paths about the longitudinal axis, wherein the venting strips have outer surfaces facing the outer covering and inner surfaces arranged to face the patient's limb; and
a set of buffers respectively arranged in the seams and following respective helical paths around the longitudinal axis;
wherein the buffers are respectively anchored to one of the adjacent pair of the venting strips located on a common side thereof relative to a first direction around the longitudinal axis to be arranged in fixed relation to each other, and wherein the buffers are free from anchoring to another one of the adjacent pair of the venting strips on a common side thereof relative to a second direction around the longitudinal axis opposite to the first direction, so as to form a plurality of subassemblies of the tubular assembly which are detached from each other, each of the subassemblies comprising one of the buffers and one of the venting strips;
wherein the venting strips and the buffers are flexible axially and angularly of the longitudinal axis to permit twisting of the tubular assembly around the longitudinal axis for varying the diameter of the tubular assembly to fit the patient's limb; and
wherein each of the buffers comprises a separation panel in a corresponding one of the seams and forming a barrier between adjacent venting strips and a shielding panel of the buffer affixed to the separation panel and disposed outside the corresponding seam and in opposite relation to the outer covering, wherein the shielding panel is disposed radially inwardly of the inner surfaces of the adjacent venting strips relative to the longitudinal axis for contacting skin of the patient's limb and maintaining the inner surfaces of the venting strips in spaced relation to the skin.

2. The venting device of claim 1, wherein at least some of the venting strips comprise fabric-spacer material.

3. The venting device of claim 1, wherein at least some of the venting strips are protrusion strips.

4. The venting device of claim 1, wherein the venting strips comprise a first subset of the venting strips including fabric-spacer material and a second subset of the venting strips in the form of protrusion strips.

5. The venting device of claim 4, wherein each of the protrusion strips includes a cover sheet and an underlying protrusion sheet, the protrusion sheet forming a plurality of protrusions and corresponding cavities.

6. The venting device of claim 1, wherein each venting strip of the set of venting strips includes a venting material strip and a tubinette envelope.

7. The venting device of claim 6, wherein the tubinette is anchored to the outer covering and the venting material strip is free to shift within the tubinette envelope.

8. The venting device of claim 1, wherein each buffer further comprises a set of mounting panels attached to the separation panel opposite the shielding panel for providing anchor points to which the outer covering is securable to the buffer.

9. The venting device of claim 1, wherein each buffer further comprises a set of mounting panels attached to the separation panel opposite the shielding panel for providing anchor points to which the outer covering is securable to the buffer.

10. The venting device of claim 1, wherein the outer covering comprises netting.

11. The venting device of claim 1, wherein the outer covering comprises loose fabric.

12. The venting device of claim 1, wherein each venting strip is anchored to the outer covering via one or more of a thread knot and an adhesive segment.

13. The venting device of claim 1, wherein each buffer is anchored to the adjacent venting strip of a common one of the interconnected subassemblies via one or more of a thread knot and an adhesive segment.

14. The venting device of claim 1, further comprising a decorative panel secured to the outer surface of the outer covering.

* * * * *